US009814815B2

(12) United States Patent
McSweeney et al.

(10) Patent No.: US 9,814,815 B2
(45) Date of Patent: Nov. 14, 2017

(54) IMPLANTABLE CONNECTOR

(71) Applicant: HeartWare, Inc., Miami Lakes, FL (US)

(72) Inventors: Timothy Michael McSweeney, South Miami, FL (US); Brad Aurilia, Coconut Creek, FL (US); Michael Tajima, Acton, MA (US)

(73) Assignee: HeartWare, Inc., Miami Lakes, FL (US)

( * ) Notice: Subject to any disclaimer, the term of this patent is extended or adjusted under 35 U.S.C. 154(b) by 56 days.

(21) Appl. No.: 14/971,311

(22) Filed: Dec. 16, 2015

(65) Prior Publication Data

US 2016/0175502 A1   Jun. 23, 2016

Related U.S. Application Data

(60) Provisional application No. 62/093,208, filed on Dec. 17, 2014.

(51) Int. Cl.
| | | |
|---|---|---|
| *A61M 1/10* | (2006.01) | |
| *A61M 1/12* | (2006.01) | |
| *H01R 13/639* | (2006.01) | |
| *H01R 24/00* | (2011.01) | |
| *H01R 24/58* | (2011.01) | |

(52) U.S. Cl.
CPC .......... *A61M 1/1008* (2014.02); *A61M 1/127* (2013.01); *H01R 13/639* (2013.01); *H01R 24/005* (2013.01); *H01R 24/58* (2013.01); *H01R 2201/12* (2013.01)

(58) Field of Classification Search
CPC ................................................ A61M 1/10008
See application file for complete search history.

(56) References Cited

U.S. PATENT DOCUMENTS

| | | |
|---|---|---|
| 4,619,640 A | 10/1986 | Potolsky et al. |
| 5,324,311 A | 6/1994 | Acken |
| 5,509,928 A | 4/1996 | Acken |
| 5,730,628 A | 3/1998 | Hawkins |
| 6,029,089 A | 2/2000 | Hawkins et al. |

(Continued)

FOREIGN PATENT DOCUMENTS

CA   2886579 A1   4/2014

OTHER PUBLICATIONS

International Search Report for Application No. PCT/US2015/066066 dated Mar. 31, 2016.

*Primary Examiner* — Suzette J Gherbi
(74) *Attorney, Agent, or Firm* — Christopher & Weisberg, P.A.

(57) ABSTRACT

A connection system implantable within a living body having an exterior skin includes a male connector and a female connector. The male connector includes a shaft extending along an axis between a proximal end and a distal end, the shaft having an exterior surface surrounding the axis, at least one shaft contact carried on the shaft and exposed at the exterior surface, and a retaining element mounted to the shaft. The female connector includes a structure defining a bore extending along an axis between a proximal end and a distal end, at least one bore contact mounted to the structure and exposed within the bore and a catch element mounted to the structure. The catch and retaining elements allow the shaft to be inserted into the bore to align the contacts. A locking element rotatably locks the shaft in the bore. A method of implanting the system is also provided.

22 Claims, 16 Drawing Sheets

(56) References Cited

U.S. PATENT DOCUMENTS

| | | |
|---|---|---|
| 6,039,685 A | 3/2000 | Bushek |
| 6,048,218 A | 4/2000 | Greenstein |
| 6,907,292 B1 | 6/2005 | Hill |
| 7,035,689 B1 | 4/2006 | Hawkins et al. |
| 8,543,209 B2 | 9/2013 | Tyers et al. |
| 8,652,024 B1 | 2/2014 | Yanai et al. |
| 8,794,989 B2 | 8/2014 | Kearsley et al. |
| 8,849,405 B2 | 9/2014 | Seeley et al. |
| 2010/0070009 A1 | 3/2010 | Barker |
| 2010/0204539 A1 | 8/2010 | Tansley et al. |
| 2010/0256440 A1 | 10/2010 | Maher et al. |
| 2011/0029052 A1 | 2/2011 | McDonald et al. |
| 2011/0275883 A1 | 11/2011 | Peters |
| 2011/0298304 A1 | 12/2011 | Cotter |
| 2012/0059443 A1 | 3/2012 | Sabin |
| 2012/0149229 A1 | 6/2012 | Kearsley et al. |
| 2014/0094645 A1 | 4/2014 | Lafontaine et al. |
| 2014/0207205 A1 | 7/2014 | Jullien et al. |
| 2014/0222111 A1 | 8/2014 | Funderburk et al. |
| 2014/0228919 A1 | 8/2014 | Seeley et al. |
| 2014/0277218 A1 | 9/2014 | Janzig |
| 2014/0285396 A1 | 9/2014 | Lee et al. |
| 2014/0303427 A1 | 10/2014 | Kerkhoffs et al. |
| 2014/0316502 A1 | 10/2014 | Seeley |

IMPLANTABLE CONNECTOR

CROSS-REFERENCE TO RELATED APPLICATIONS

The present application claims the benefit of the filing date of U.S. Provisional Application No. 62/093,208, filed Dec. 17, 2014, entitled IMPLANTABLE CONNECTOR, the disclosure of which is hereby incorporated herein by reference.

BACKGROUND OF THE INVENTION

The present invention relates to an implantable connector for use with a medical device implanted within an animal; or, more particularly, for use with an implanted ventricular assist device and system.

In certain disease states, the heart lacks sufficient pumping capacity to maintain adequate blood flow to the body's organs and tissues. For example, conditions such as ischemic heart disease and hypertension may leave the heart unable to fill and pump efficiently. This condition, also called congestive heart failure, may lead to serious health complications and even death. In fact, congestive heart failure is one of the major causes of death in the Western world.

This inadequacy of the heart can be alleviated by providing a mechanical pump also referred to as a ventricular assist device ("VAD") to supplement the pumping action of the heart. VADs may be used to assist the right ventricle, the left ventricle, or both. For example, a VAD may assist the left ventricle by mechanically pumping oxygenated blood from the left ventricle into the aorta. In this case, the pump is implanted within the body of the patient so that an inflow opening of the pump communicates with the left ventricle, and an outflow opening of the pump communicates with the aorta. The pump receives blood from the left ventricle and then pushes it into the aorta for distribution throughout the body. This reduces the strain on the heart by reducing the volume of blood that the heart is responsible for moving. A VAD having an inflow opening communicating with the right ventricle and an outflow opening communicating with a pulmonary artery may be used to assist the right ventricle.

U.S. Pat. Nos. 7,575,423, 7,976,271, 8,007,254, and 8,419,609, the disclosures of which are hereby incorporated by reference, disclose certain rotary blood pumps which can be used as ventricular assist devices. These pumps are electrically powered. Typically, these and other electrically powered implantable pumps are connected through a cable, commonly referred to as a "driveline," to a control device which supplies electric power to the pump and controls its operation. The control device is often external to the patient's body, in which case the driveline must extend out of the body via a skin opening. The control device must usually provide continuous electric power over the driveline. This power must be provided at relatively high current (0.5-2.0 Amps) and moderate voltage (3-40 Volts) for extended periods of time, such as years or decades, without losing electrical continuity and creating heat losses due to resistance that would cause physiological complications.

The driveline must withstand movement of the surrounding body tissues and contamination by body fluids. Separable connectors generally have been regarded as not providing the requisite combination of current carrying capacity, reliability and durability in this demanding environment. The drivelines used heretofore typically have been made as continuous cables, without any separable connections at least in that portion of the driveline that extends within the body of the patient.

Because any skin opening provides a natural means for bacteria or other contaminants to enter the body, infections can occur at the skin opening. If such an infection occurs, then it may become necessary to remove or replace the driveline from the skin opening to permit proper treatment of the infection. Where the driveline is a continuous element, there is presently no way to effect these treatments without subjecting the patient to a major surgery. Typically, a surgeon must remove the entirety of the existing driveline, including the portion adjacent the VAD, in order to route the new driveline through a new skin opening that is remote from the infection.

It has also been proposed to use implanted control devices that receive power from an external source by means of an implanted induction coil, without a permanent skin-penetrating connection. In such an arrangement, the control device and the entire driveline are disposed within the body. It would be desirable to provide a separable connector at one or both ends of such a driveline to facilitate threading of the driveline through the body during installation.

Therefore, further need exists for improvements in drivelines and connection systems.

BRIEF SUMMARY OF THE INVENTION

A first aspect of the present invention is a connection system implantable within a living body having an exterior skin. The system includes a male connector with a shaft extending along an axis between a proximal end and a distal end, the shaft having an exterior surface surrounding the axis, at least one shaft contact carried on the shaft and exposed at the exterior surface, and a retaining element mounted to the shaft. The system further includes a female connector with a structure defining a bore extending along an axis between a proximal end and a distal end, at least one bore contact mounted to the structure and exposed within the bore and a catch element mounted to the structure. The catch and retaining elements are constructed and arranged so that the shaft can be inserted into the bore along the axis of the bore to align the at least one shaft contact with the at least one bore contact. The shaft can be inserted in the bore in a first position in which the retaining element is offset from the catch element and retained in the bore when rotated about the axis of the bore into a second position in which the retaining element is aligned with the catch element. A locking element is mounted to one of the shaft and the structure, the locking element being movable between an unlocked position in which the shaft can be rotated about the axis of the bore and a locked position in which the locking element prevents rotation of the shaft relative to the structure.

In accordance with other embodiments of the first aspect, the bore may be closed at its distal end and the male and female connectors may be constructed and arranged to seal the bore proximal to the at least one bore contact when the shaft is inserted in the bore. The male and female connectors may cooperatively define a sealed interior volume when the shaft is inserted in the bore, wherein the sealed interior volume is at least about 1.10 times the volume of the shaft disposed within the sealed volume when the male and female connectors are fully engaged with one another. The structure may define an expansion space in communication with the bore, and the expansion space may be at least about 0.05 times the total interior volume.

The catch element may include a catch ring with proximal and distal surfaces extending at least partially around the axis of the bore, the catch ring having at least one groove extending from the proximal surface to the distal surface, and the retaining element may include at least one projection extending away from the exterior surface of the shaft transverse to the axis of the shaft such that the at least one projection can be inserted through the at least one groove. The system may further include an anti-rotation element mounted to the structure and disposed distal to catch ring, the anti-rotation element configured to engage the at least one projection to limit rotation of the shaft relative to the structure. The structure may define a hole extending into the bore transverse to the axis of the bore, and the locking element may be engageable with the male connector through the hole to lock the shaft against rotation relative to the structure. The locking element may be a set screw and the hole may have a threaded wall, and a driving portion of the set screw may be covered by a set screw seal adapted to receive a tool engageable with the driving portion.

Either the shaft or the bore may have at least one seal adapted to seal the bore proximal to the at least one bore contact when the shaft is inserted in the bore. The at least one shaft contact may include a first set of shaft contacts spaced apart from a second set of shaft contacts along the axis of the shaft and the at least one bore contact may include a first set of bore contacts spaced apart from a second set of bore contacts along the axis of the bore, wherein insertion of the shaft into the bore along the axis of the bore aligns the first and second sets of shaft contacts with the respective first and second sets of bore contacts. The system may further include an intermediate seal on either the shaft or the bore, the intermediate seal being disposed between the first and second sets of shaft and bore contacts when the shaft contacts are aligned with the bore contacts. Each of the first and second sets of shaft contacts the each of the first and second sets of bore contacts may include three contacts. Either the shaft or the bore may have at least one seal located between each mutually adjacent shaft or bore contact. The system may further include an implanted medical device having first and second elements, the second element being sufficient to sustain life, and wherein the first element is connected to the first sets of shaft and bore contacts, the second element is connected to the second sets of shaft and bore contacts. Each of the first and second elements may be a pump having a motor.

The at least one shaft contact may be an outer ring and the at least one bore contact may be an inner ring, the inner ring being coaxially aligned with the outer ring when the male connector is inserted into the female connector. The system may further include an elongated conductor with a terminus attached to each of the at least one bore contacts and the at least one shaft contacts, wherein each terminus is welded to a respective swage cap that is conductively attached to the respective elongated conductor. Each of the at least one bore contacts may have an interior surface with an annular groove and a spring element disposed in the annular groove so as to conductively engage one of the at least one shaft contacts.

A second aspect of the present invention is a connection system implantable within a living body having a thorax and an exterior skin. The system includes a first driveline extending between an implantable device configured to be located inside the thorax and a first connector configured to be located at an internal connection point disposed outside of the thorax, and a second driveline configured to extend through the exterior skin between an external device located outside the body and a second connector that is configured to be releasably coupled to the first connector at the internal connection point so as operatively connect the first and second drivelines, wherein the first connector can be decoupled from the second connector at the internal connection point.

In accordance with other embodiments of the second aspect, the internal connection point may be disposed outside of the pericardial sac. The implanted device may be a medical device having at least two partially redundant elements, each element being sufficient to sustain life, wherein each of the first and second connectors has a first set of contacts sealed independently from second set of contacts, and wherein each of the at least two partially redundant elements is powered by one of either the first or second set of contacts. The second driveline may be configured to extend between the second connector at the internal connection point and a third connector adapted for mounting at the skin.

A third aspect of the present invention is a method of implanting a connection system within a living body having a thorax and an exterior skin, including implanting a device in the body and locating a first connector of a first driveline attached to the device at an internal connection point disposed outside of the thorax, releasably coupling a second connector of a second driveline to the first connector at the internal connection point to operatively connect the first and second drivelines, and installing the second driveline so that a portion of the second driveline extends through the skin.

In accordance with other embodiments of the third aspect, the method may further include the steps of releasably decoupling the first connector from the second connector at the internal connection point, releasably coupling a third connector of a third driveline to the first connector at the internal connection point so as operatively connect the first and third drivelines, and installing the third driveline so that a portion of the third driveline extends through the skin. The second driveline may extend through the skin a first exit point, and the third driveline may extend through the skin at a second exit point remote from the first exit point.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1A:
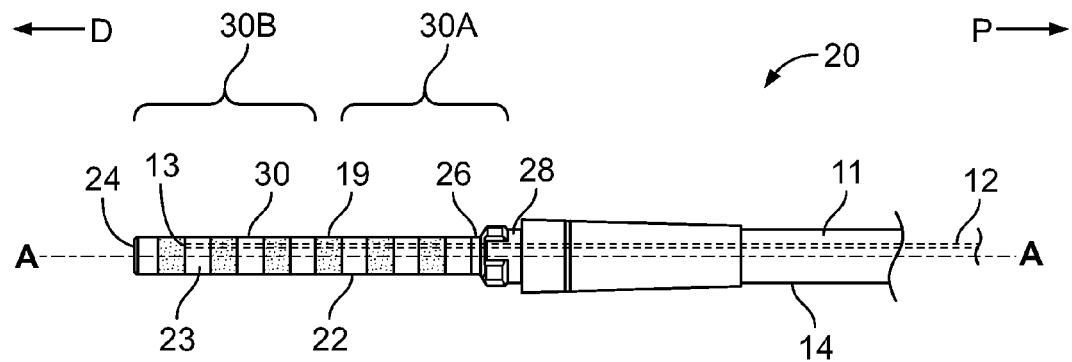
FIGS. 1A and 1B are front plan views of a male connector and a female connector, respectively, of a connection system in accordance with one embodiment of the present invention.
Figure 1B:
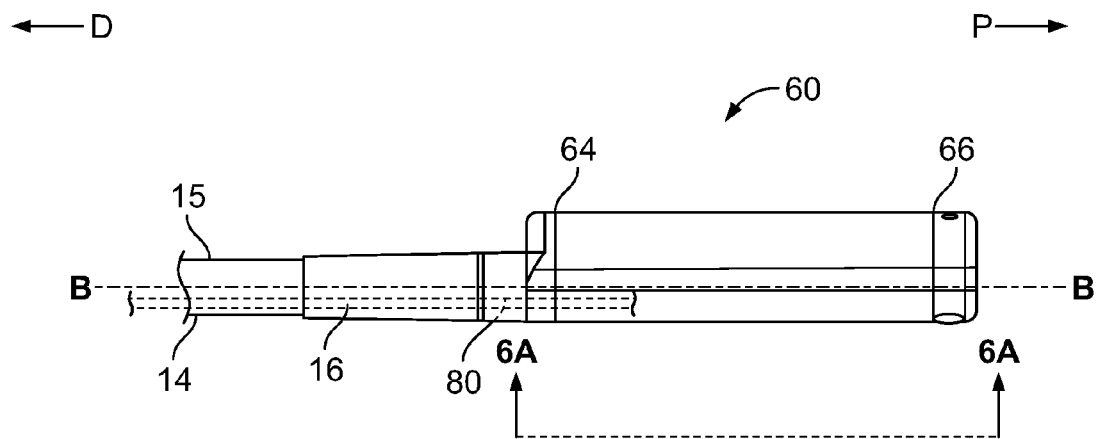
Figure 11A:
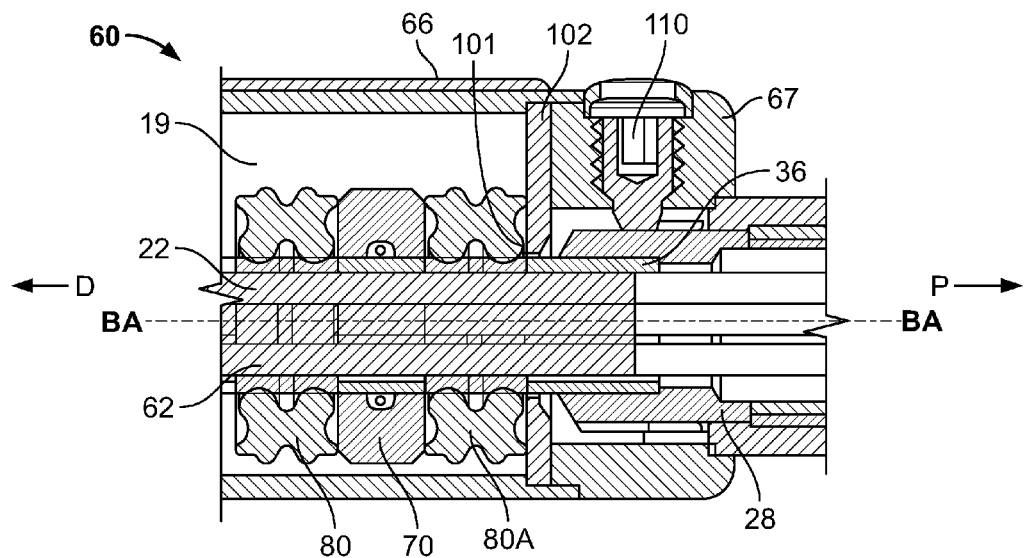
FIGS. 11A and 11B are front sectional views of different portions, respectively, of the male connector shown in FIG. 1A assembled with the female connector shown in FIG. 1B.

FIGS. 1A and 1B illustrate elements of a connection system 10 that, for example, may be an element of an implanted VAD system in accordance with the present invention. As shown, system 10 includes a male connector 20 that is mateable with a female connector 60. Male connector 20 is attached to a male or first driveline 11, while female connector 60 is attached a female or second driveline 15. Thus, system 10 conductively attaches, i.e., permits electricity to flow between, the first and second drivelines 11 and 15 once male connector 20 is received within female connector 60. As described in detail below, male connector 20 extends along an axis A-A, while female connector 60 extends along an axis B-B. When the connectors 20 and 60 are engaged with one another, these axes are coaxial with one another. The designation BA-BA is used in the drawings (e.g., FIG. 11A) to denote the coaxial axes A-A and B-B.

Male connector 20 has a shaft 22 extending along axis A-A between a distal end 24 and a proximal end 26. For simplicity, each of the proximal and distal directions have been labeled with a respective "P" and "D" arrow in the drawings to permit consistent use of those terms with respect to male and female connectors 20, 60 and the related methods and systems described herein. Shaft 22 has an exterior surface 23 surrounding axis A-A with a diameter sized for insertion into a bore 62 (FIG. 6A) of female connector 60.

Shaft 22 has at least one shaft contact 30 carried on shaft 22 and at least partially exposed at exterior surface 23. Although depicted as circular, shaft contacts 30 may assume any number of geometric forms. In the depicted embodiment, each shaft contact 30 is a conductive ring, best seen in FIGS. 2A and 2B, with a diameter 30D. The remainder of shaft 22 has a diameter equal to the diameter 30D of the shaft contacts. Shaft 22 may have a plurality of shaft contacts 30, spaced apart from one another along axis A-A. In the depicted embodiment, shaft 22 has six shaft contacts 30 that are spaced apart along axis A-A, each shaft contact 30 being separated from the next adjacent shaft contacts by a potting material 19 discussed in detail below.

Figure 4:
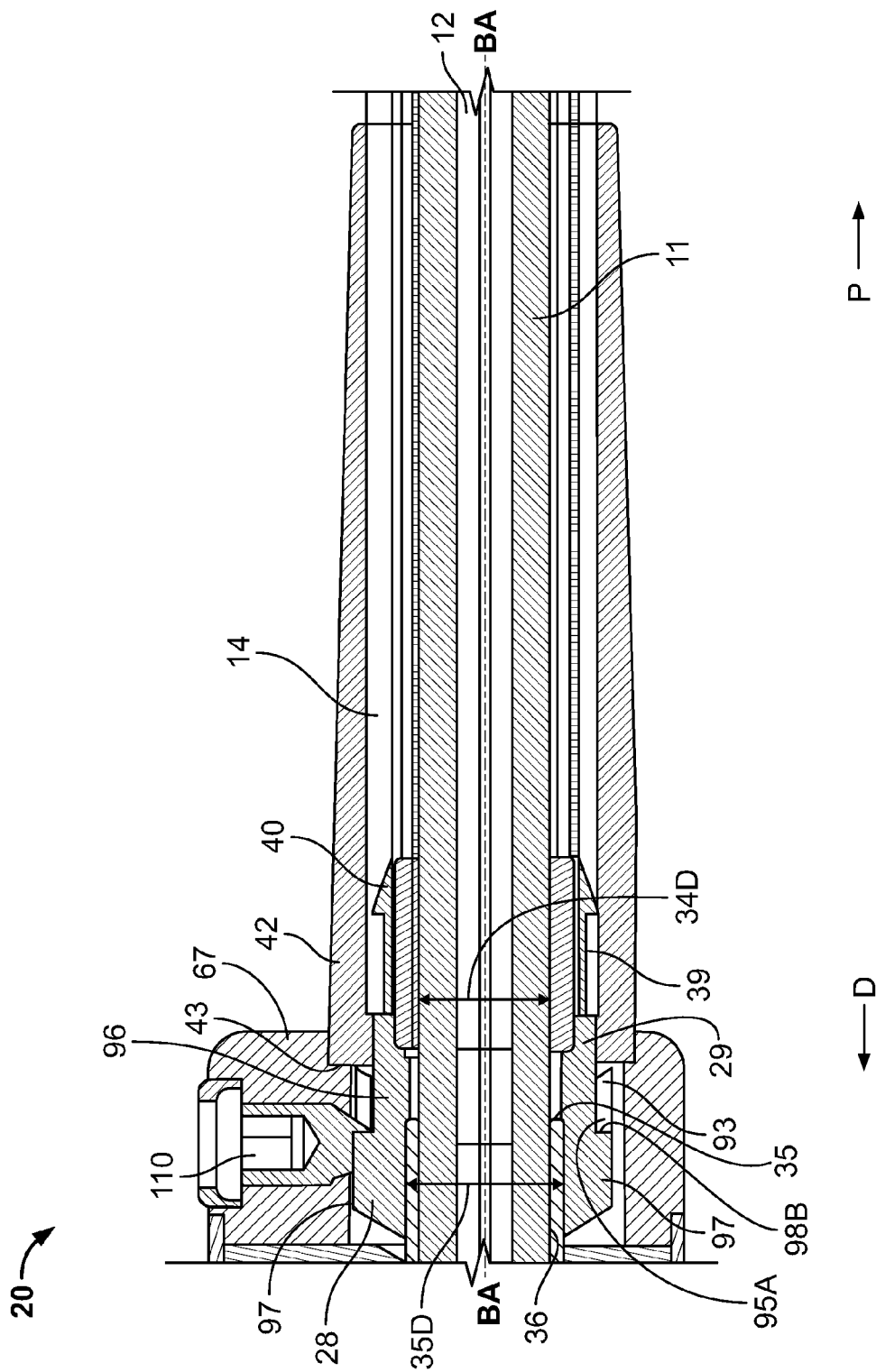
FIG. 4 is a front sectional view of a first driveline of the male connector shown in FIG. 1A.

First driveline 11 is attached to a male driveline interface 28 located adjacent to proximal end 26 of shaft 22. Driveline 11 is a cable that includes at least one first elongated conductor 12, one of which is depicted as broken lines in FIG. 1A. Each conductor 12 preferably includes a conductive core covered by a thin insulating layer. For example, each elongated conductor 12 may be a wire with a conductive core made of silver. As shown in FIG. 4, first driveline 11 includes a first exterior housing 14 that surrounds each first elongated conductor 12 along at least a portion of its length. First exterior housing 14 is preferably made of a flexible, implantable material, such as a material derived from polyurethane, polyvinyl chloride, silicone, nylon, or other biocompatible material with like properties.

Figure 2A:
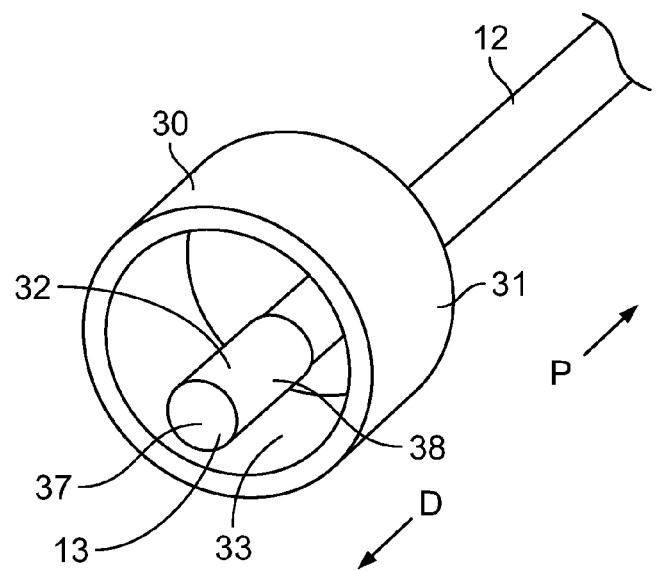
FIGS. 2A and 2B are front perspective and top plan views, respectively, of a shaft contact, an elongated conductor, and a swage cap of the male connector shown in FIG. 1A.
Figure 2B:
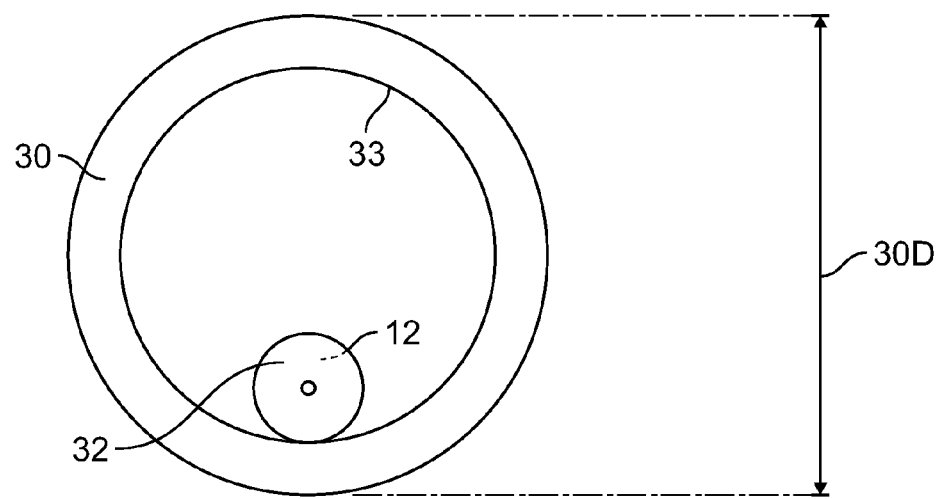

Each elongated conductor 12 extends from first driveline 11, through male driveline interface 28, and into the interior of shaft 22. A first terminus 13 of each first elongated conductor 12 is adjacent to a particular shaft contact 30, as best seen in FIG. 1A. Generally, each conductor 12 extends co-directionally with axis A-A. Each shaft contact is conductively attached to one of the first elongated conductors 12 within shaft 22. Preferably, each shaft contact 30 is made of a weldable material such as platinum, platinum-iridium alloy, or other conductive metal that can be laser welded, resistance welded, or likewise fused with an elongated conductor 12. An exemplary first elongated conductor 12 is depicted in FIG. 2A as being lap welded to an interior surface of shaft contact 30. To facilitate welding and mitigate corrosion risks, first terminus 13 of first elongated conductor 12 is covered with a swage cap 32 having a chamfered front face 37 and an elongated body 38. One swage cap 32 is crimped, swaged, welded, or otherwise conductively attached to each first elongated conductor 12. The metal of swage caps 32 is selected for compatibility with shaft contacts 30. Preferably, a portion of elongated body 38 of swage cap 32 is lap welded to interior surface 33 of shaft contact 20, as shown in FIG. 2B. By virtue of this configuration, swage cap facilitates welding and mitigates the corrosion risks associated with welding dissimilar metals, such as, for example, the platinum of the contacts and the silver cores of the exemplary wires described above.

FIG. 1A also shows that each shaft contact 30 is at least partially surrounded on at least one side by a backfill or potting material 19. Preferably, potting material 19 has a high dielectric strength. Potting material 19 desirably is also an adhesive material capable of bonding with each shaft conductor 30 to form shaft 22. For example, potting material 19 may be an epoxy, polymeric resin, or thermoplastic polymer, such as polyketone or like material. As described with reference to the methods of manufacture set forth below, potting material 19 is preferably a flowable material selected to optimize the flexural and tensile strengths of male and female connectors 20, 60.

Figure 3A:
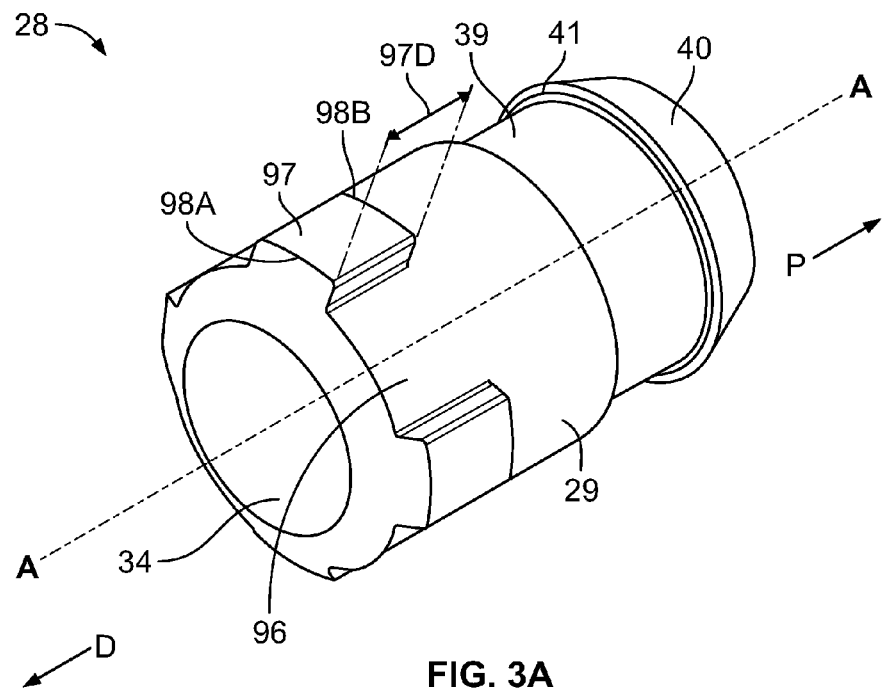
FIGS. 3A and 3B are front perspective and top plan views, respectively, of a male driveline interface of the male connector shown in FIG. 1A.

An exemplary embodiment of male driveline interface is depicted in FIG. 3A. As shown, interface 28 is preferably a hollow, generally cylindrical element having an exterior surface 29 extending along axis A-A from an entry portion 34 to an annular ridge 40 that is adapted to engage driveline 11. Entry portion 34 is adjacent to the distal end of male driveline interface 28, and defines an internal diameter 34D.

Figure 3B:
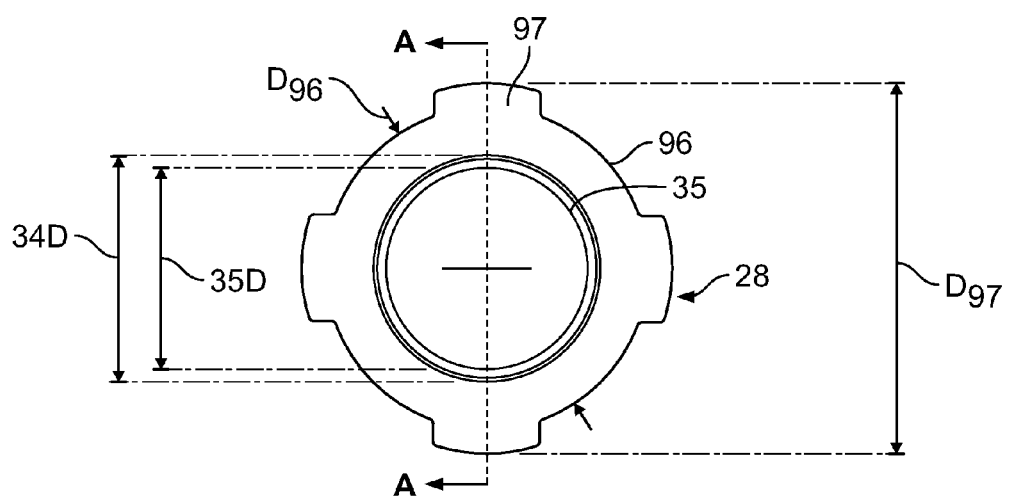

Male driveline interface 28 defines a slightly smaller internal diameter 35D at its proximal end, and a lip 35 at the juncture of diameters 35D and 34D. Diameter 35D is sized to receive at least one first elongated conductor 12 therein. For example, the smaller inner diameter 35D of male driveline interface 28 in FIG. 3B is approximately 3 to 6 mm and sufficient to house six elongated conductors 12 therein. Diameter 34D sized to receive a guiding element 36 at proximal end 26 of shaft 22. Guiding element 36 is coaxial with shaft 22 and has an outer diameter approximately equal to the outer diameter of shaft 22. Preferably, guiding element 36 is an elongated titanium ring engageable with a corresponding element of female connector 60 to guide shaft 22 into bore 62, as described in detail below.

The distal end of male driveline interface 28 has a retaining portion 96 located adjacent to proximal end 26 of shaft 22. FIG. 3B depicts an exemplary arrangement of retaining portion 96 having four retaining projections 97. The retaining projections 97 are arranged in an array on exterior surface 29 of male driveline interface 28. In the embodiment depicted, the projections 97 are spaced apart from one another about the circumference of the driveline interface.

Figure 5A:
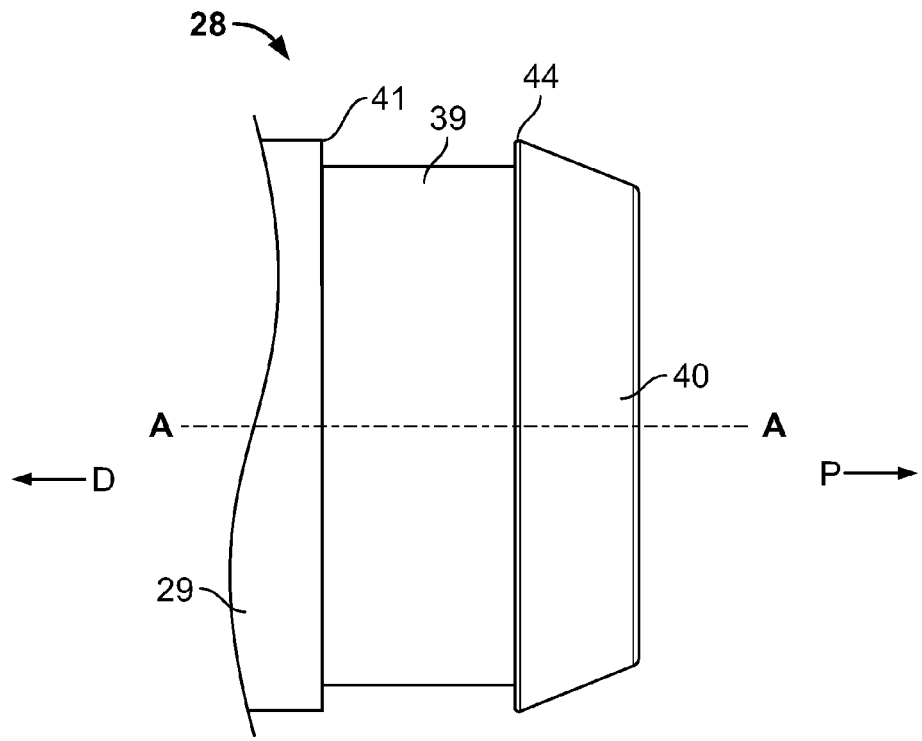
FIGS. 5A and 5B are front plan views of different versions, respectively, of a proximal end of the male driveline interface shown in FIGS. 3A and 3B.
Figure 5B:
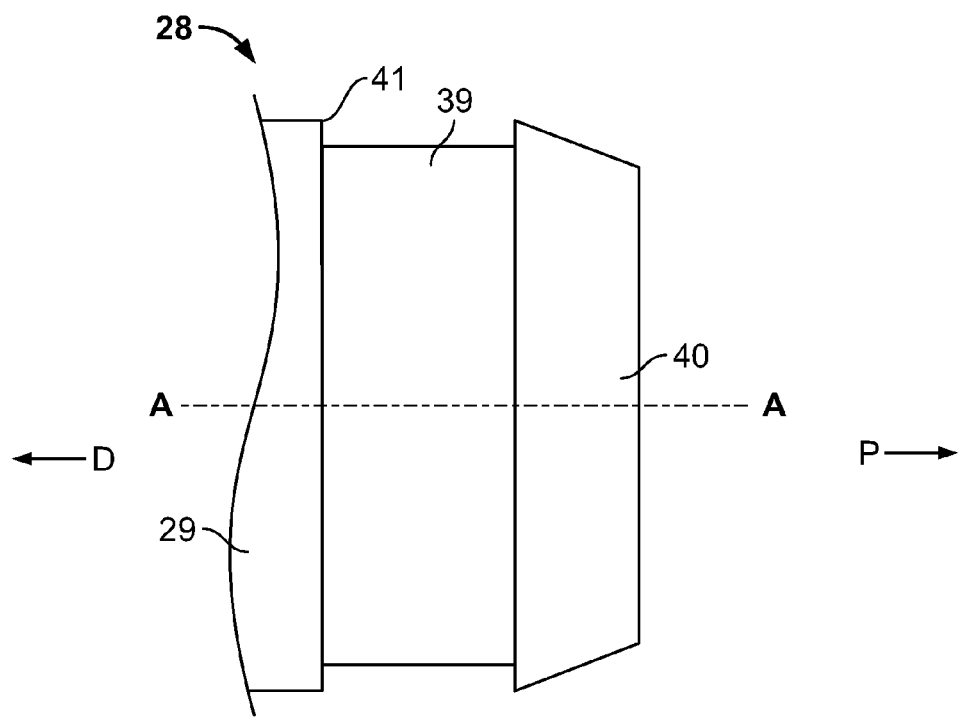

The proximal end of male driveline interface 28 is depicted in FIGS. 5A-B as having a depression 39 and annular ridge 40. Depression 39 is an indented potion of exterior surface 29 that extends around axis A-A between a ledge 41 defined by an annular ridge 40. Annular ridge 40 preferably has a triangular cross-section and defines a surface of revolution about axis A-A. For example, annular ridge 40 is shown in FIG. 5B as having a triangular cross-section with a height extending away from axis A-A. Alternatively, as in FIG. 5A, annular ridge 40 may also have a cylindrical portion 44. Ridge 40 of the male driveline interface 28 is adapted to engage exterior housing 14 of first driveline 11. Preferably, the elements described above permit male driveline interface to be securely engaged to exterior housing 14 to meet industry standard requirements for tensile and flexural strength.

To provide additional tensile and flexural support, an overmold 42 preferably covers the entirety of the proximal end of male driveline interface 28, including depression 39 and ridge 40. As shown in FIG. 4, overmold 42 tapers away from an edge portion 43 in the proximal direction along axis A-A. As further discussed below, edge portion 43 forms a seal with the female connector when the connectors are engaged with one another. In addition, overmold 42 also mechanically supports the connection system by providing a means of strain relief for first driveline 11, and by compressively reinforcing the connection between male driveline interface 28 and exterior housing 14 of first driveline 11. Lastly, overmold 42 also provides male connector 20 with a streamlined exterior profile that is easily pulled through a surgically formed tunnel in the body during installation of the driveline.

Figure 13:
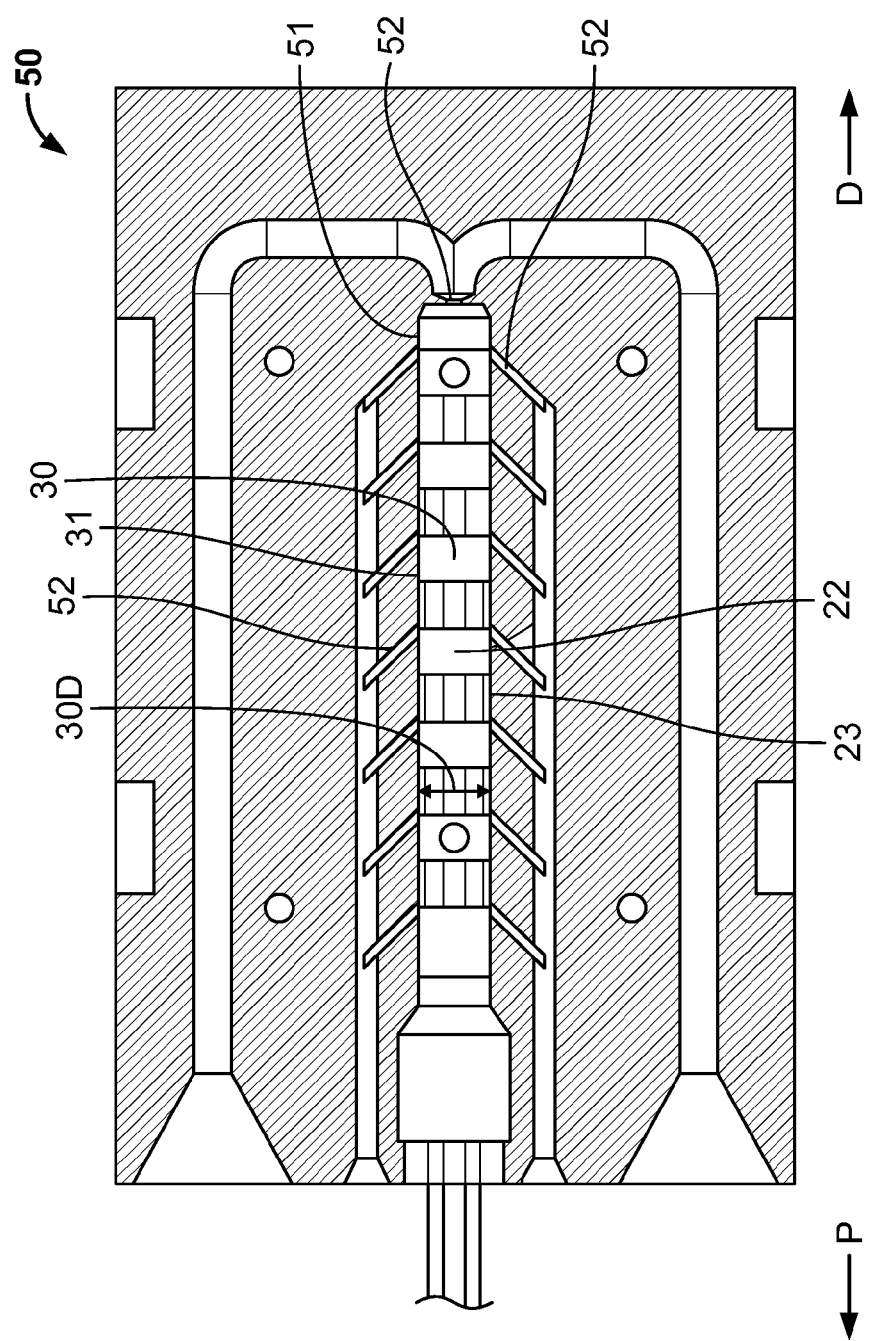
FIG. 13 is a top plan view of a mold and components of the male connector shown in FIG. 1A.

The elements of male connector 20 set forth above may be assembled using the exemplary manufacturing method shown by FIG. 13. As shown, this method uses a mold 50 that is adapted to form shaft 22. The elements of shaft 22, including shaft contacts 30 and driveline interface 28, are positioned in a spaced apart arrangement within a main channel 51 of mold 50. Each shaft contact 30 is conductively attached to at least one first elongated conductor 12, preferably using swage cap 32, prior to arrangement within mold 50. After all the elements of male connector 20 have been attached and arranged, the potting material 19 (FIG. 1A) is guided into the spaces between the shaft elements of shaft 22 by a plurality of channels 52 on mold 50. Once guided into position, potting material 19 is cured into its final, relatively hardened state. Where the potting material is an epoxy or other chemically reactive composition, curing occurs by chemical reaction, with or without application of heat. Where the potting material is a thermoplastic, curing may occur by cooling of the potting material. Mold 50 preferably makes the exterior surface of potting material 19 flush or nearly flush with the exterior surface 31 of each shaft contact 30 so as to ensure that diameter 30D is constant along shaft 22, as in FIG. 1A. To ensure a smooth exterior surface for optimum connection with female connector 60, exterior surface 23 of shaft 22 may subjected to a method of surface treatment that comprises, for example, the step of grinding or otherwise machining the exterior surface 23 of shaft 22 until it has a constant diameter 30D. This step may also provide a desired surface finish on the exterior surface 31 of each shaft contact 30, and to assure that there is no potting material overlying the exterior surfaces of the shaft contacts.

Figure 6A:
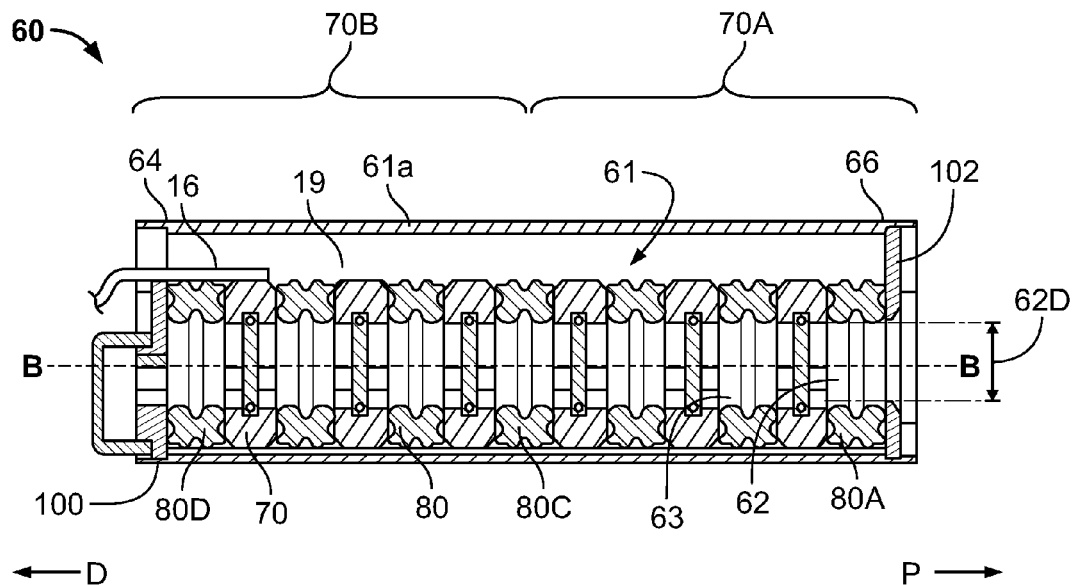
FIG. 6A is a front sectional view a proximal portion of the female connector shown in FIG. 1B.
Figure 6B:
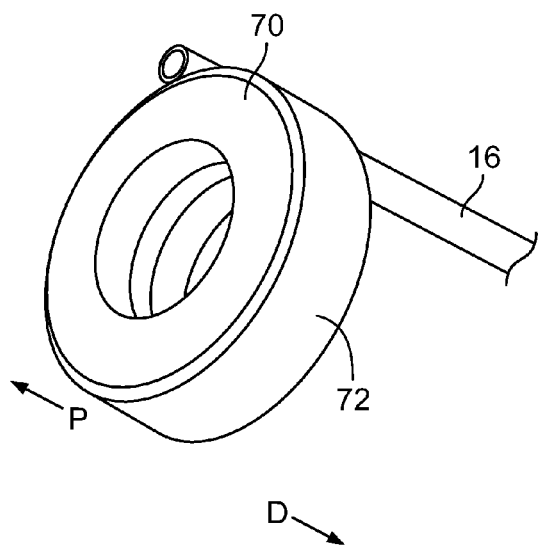
FIG. 6B is a front perspective view of a bore contact and an elongated conductor of the female connector shown in FIG. 1B.

Female connector 60 has a structure 61 defining a bore 62 extending along an axis B-B between a distal end 64 and a proximal end 66, as shown in FIG. 1B and the corresponding sectional view FIG. 6A. Bore 62 is open at proximal end 66 and closed at distal end 64. Structure 61 may include an external housing 61a shown in FIG. 1B, which is preferably made of an implantable metal. Bore 62 of female connector 60 in FIG. 6A has an interior surface 63 surrounding axis B-B. Bore 62 preferably has a diameter 62D sized to receive diameter 30D of shaft contact 30 therein. At least one bore contact 70 is mounted in structure 61 and exposed to interior surface 63 of bore 62. Like shaft contact 30, bore contact 70 may assume any number of geometric forms. For example, as in FIG. 6B, bore contact 70 may be a conductive ring 70. Like male connector 20, female connector 60 may also have a plurality of bore contacts 70, each being spaced apart along axis B-B. In this example, FIG. 6A depicts a bore 62 having six bore contacts 70.

Figure 11B:
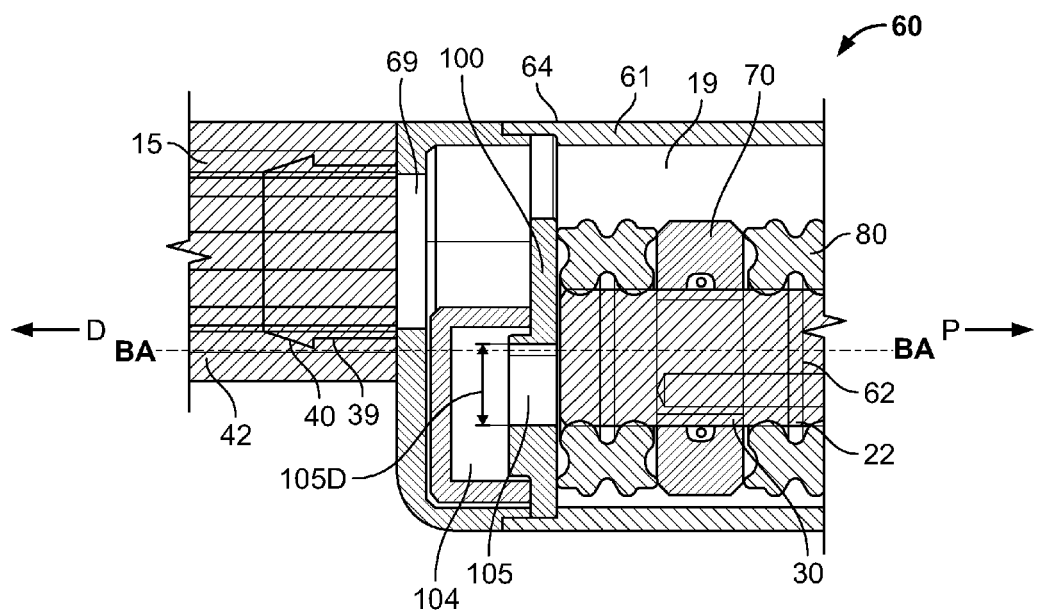

FIG. 1B also shows that a second driveline 15 is preferably attached to a female driveline interface 69 located adjacent to distal end 64 of bore 62. In FIG. 11B, the proximal end of interface 69 is integral with structure 61, although it could also be attached thereto. Similar to above, the distal end of female driveline interface 69 also has a depression and annular ridge (not shown) similar to the depression 39 and ridge 40 of the male driveline interface described above with respect to FIGS. 5A and 5B. The second driveline 15 is also a cable that includes at least one second elongated conductor 16, one of which is depicted as broken lines in FIG. 1B. Female driveline 15 preferably has an exterior housing equivalent to exterior housing 14 of male driveline 11 discussed above. The second driveline is engaged with the distal end of female driveline interface 69 in a manner similar to the engagement of the first driveline and the male driveline interface. Here again, an overmold similar to overmold 42 discussed above with reference to FIG. 4 covers the second driveline and the interface. Each second elongated conductor 16 extends generally co-directionally along axis B-B from female driveline 15, through female driveline interface 69, and into structure 61 until a second terminus 17 of each second elongated conductor 16 is adjacent to a bore contact 70 within structure 61.

Each bore contact 70 is conductively attached to at least one second elongated conductor 16. Preferably, like shaft contact 30, each bore contact 70 is also made of a weldable material such as platinum, platinum-iridium alloy, or like conductive metal that can be laser welded, resistance welded, or likewise fused with an elongated conductor 16.

Figure 7A:
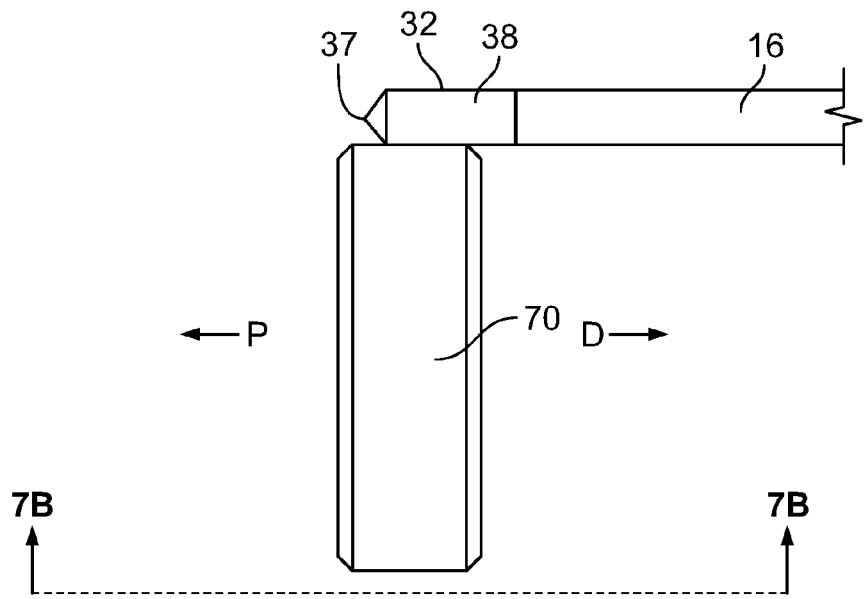
FIGS. 7A and 7B are front plan and front sectional views, respectively, of a bore contact, an elongated conductor, and a swage cap of the female connector shown in FIG. 1B.
Figure 7B:
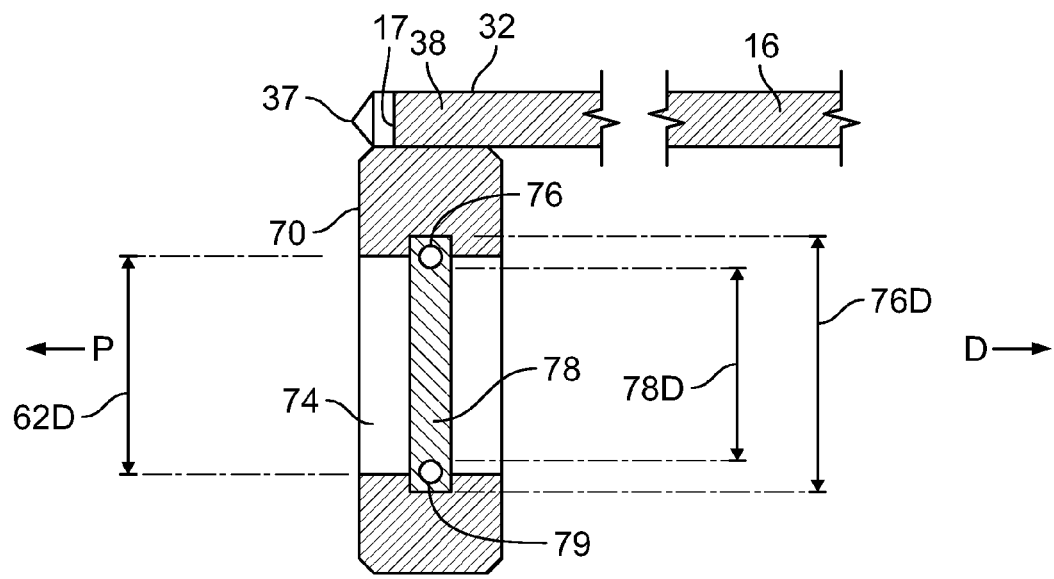

As an example, second elongated conductor 16 is depicted in FIGS. 7A and 7B as being lap welded to an exterior surface 72 of bore contact 70. Like first terminus 13, second terminus 17 of second elongated conductor 16 may be covered with a swage cap like swage cap 32. As above, a portion the swage cap may be lap welded to exterior surface 72 along a line parallel to axis B-B.

An interior surface 74 of each bore contact 70 may be optimized to conductively engage outer surface 31 of shaft contact 30. For example, interior surface 74 may be intentionally roughened to optimize its conductive potential with exterior surface 31 of shaft 22. The exemplary embodiment of FIGS. 7A-B has an interior surface 74 with an annular groove 76 extending around at least a portion of diameter 62D of bore 62. Annular groove 76 has a diameter 76D sized to receive a conductive element 78, such as conductive annular spring 78. As shown in FIG. 7B, diameter 76D is preferably greater than diameter 62D so as to define annular groove 76. Conversely, conductive spring 78 preferably has a diameter 78D that is less than diameter 30D of shaft contacts 30. By virtue of this configuration, at least a portion of conductive element 78 will remain conductively engaged with both shaft contact 30 and bore contact 70 when shaft 22 is inserted into bore 62. Likewise, when embodied as annular spring 78, diameter 78D may also provide an interference fit between shaft 22 and bore 62.

Bore contacts 70 may be secured in structure 61 by various means. For example, structure 61 may have a dielectric material defining an internal surface that is adapted to receive a corresponding outer surface of each conductor ring 70. Preferably, as in FIG. 6A, a dielectric potting material is utilized to form at least part of structure 61 and secure each bore contact 70 within bore 62. Preferably still, potting material 19 fills substantially all any space within structure 61 that is not otherwise occupied by any of the elements or spaces of female connector 60 described herein.

The female connector further includes at least one seal 80 adapted to seal bore 62 when shaft 22 is inserted into bore 62. For example, in FIG. 6A, seven seals 80 are provided in the female connector. The seals 80 include seals disposed between each pair of mutually-adjacent bore contacts 70, a seal 80D disposed distal to the bore contact 70 at the distal end of the bore, and a further seal 80A disposed proximal to the bore contact 70 at the proximal end of the bore. Seal 80A is referred to herein as the proximal end seal. One of the seals 80C is referred to herein as a center seal. Center seal 80C is disposed between the third and fourth bore contacts, so that a first set 70A including three bore contacts 70 lies proximal to the center seal, whereas a second set 70B including three bore contacts lies distal to the center seal.

Figure 8A:
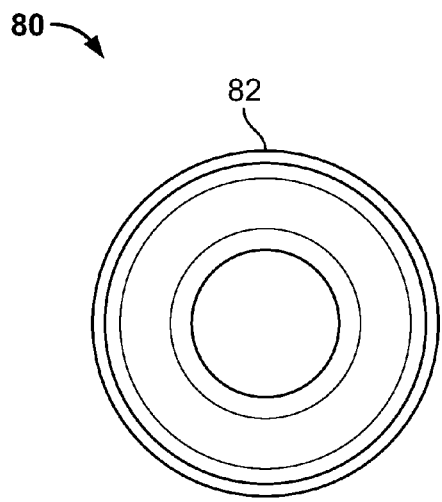
FIGS. 8A and 8B are front plan and side sectional views, respectively, of a primary seal used in connection with the female connector shown in FIG. 1B.
Figure 8B:
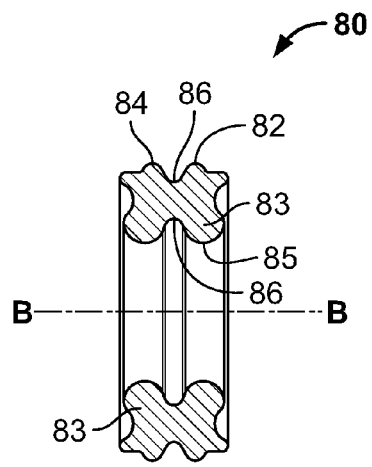

Preferably, each seal 80 is a generally circular ring formed from a soft a dielectric material such as silicone. The configuration of each seal 80 is illustrated in FIGS. 8A-B, which depicts a seal 80 that has been adapted to both seal bore 62 from immediate fluid ingress and contamination and conductively insulate each bore contact 70 from the next. For this purpose, each seal 80 preferably has an outer surface 82 with a cross-section 83 shaped to have enhanced sealing capabilities. For example, outer surface 82 in FIG. 8B has an outer circumferential surface 84 opposite of an inner circumferential surface 85. Each of these surfaces 84 and 85 desirably is a surface of revolution about axis B-B, and each of these surfaces desirably has at least one undulation 86 adapted prevent fluid entry into bore 62.

Figure 9A:
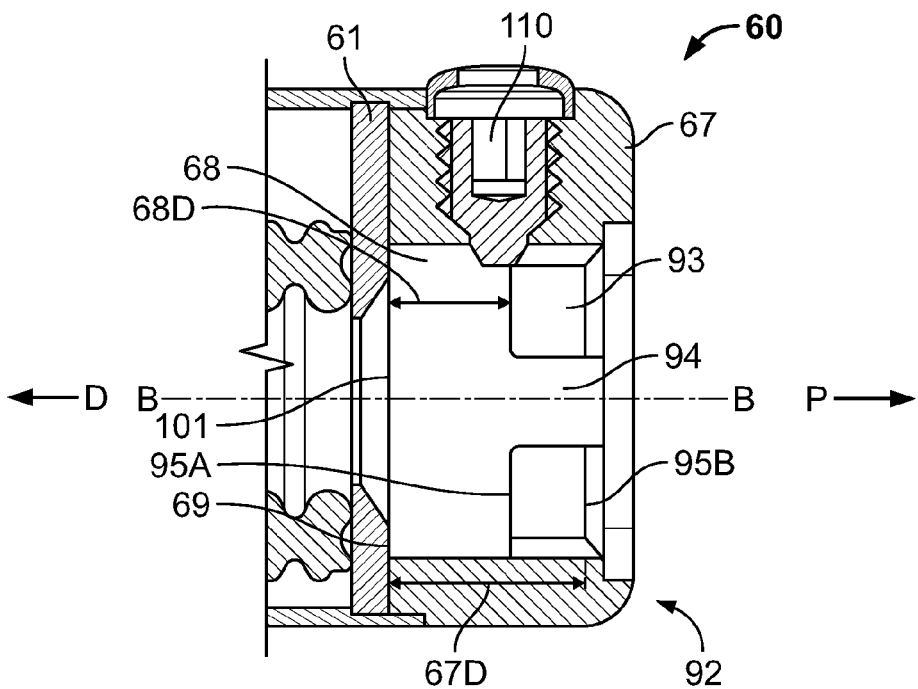
FIGS. 9A and 9B are front sectional and bottom plan views, respectively, of a proximal end of the female connector shown in FIG. 1B.
Figure 9B:
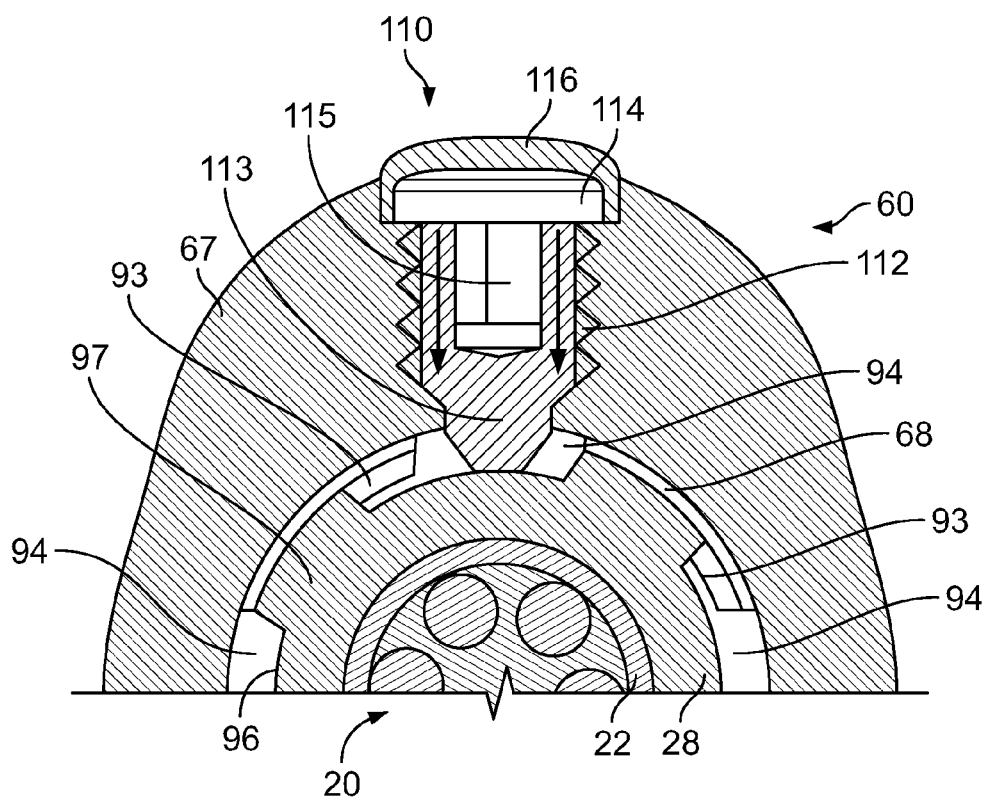

The female connector also includes a shaft receiving part 67 (FIGS. 9A-11A) disposed at the proximal end of the female connector structure 61. Shaft receiving part 67 is preferably made of a metallic material. A retention means is also provided to retain shaft 22 within bore 62. The retention means 90 includes a catch portion 91 on the shaft receiving part 67 of the female connector 60 that is engageable with retaining portion 96 (FIGS. 3A and 3B) of male connector 20. As shown in FIG. 9A, the shaft receiving part 67 defines a generally cylindrical interior bore 68 coaxial with bore 62 and with axis B-B. A catch portion in the form of a catch ring 92 projects inwardly toward towards axis B-B from of the wall of bore 68. Catch ring 92 is subdivided by grooves 94 into a set of four catch projections 93 extending inwardly toward axis B-B to define; with a groove 94 disposed between each pair of adjacent catch projections 93. Grooves 94 extend entirely through the catch ring 92 in the proximal-to-distal direction, and thus extend between the proximal faces 95B and distal faces 95A of catch projections 93. Catch projections 93 define a minor diameter smaller than the diameter of bore 68. The minor diameter defined by catch projections 93 is smaller than the major diameter $D_{97}$ defined by projections 97 on the retaining portion of the male driveline interface (FIG. 3B) However, the minor diameter defined by projections 93 is slightly larger than the minor diameter $D_{96}$ of retaining portion 96. The major diameter at grooves 94 is slightly larger than the major diameter $D_{97}$ defined by the projections on the retaining portion of the male driveline interface.

Figure 10A:
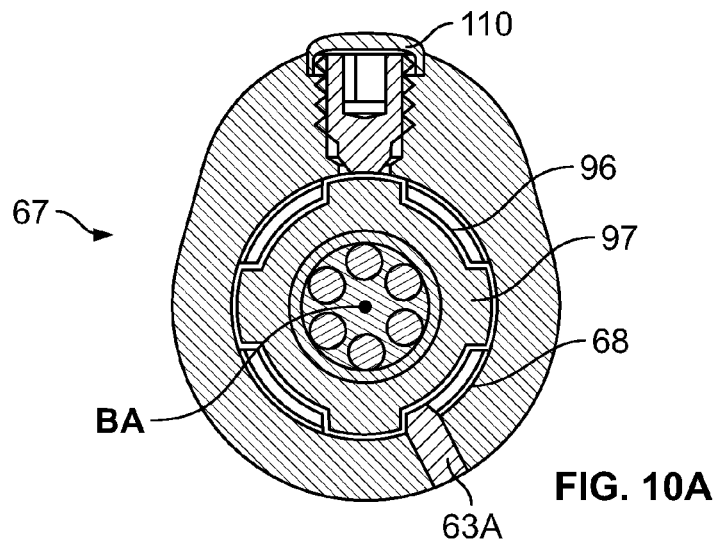
FIGS. 10A-10C are bottom plan views of the female connector shown in FIG. 1B.

Catch ring 92 is adapted to correspond with retaining portion 96 of male connector 20. For example, grooves 94 and catch projections 93 are preferably spaced apart around the circumference of catch ring 92 so that the spacing of grooves 94 corresponds with the spacing of retaining portions 97 (FIG. 3A) on retaining portion 96 of male connector 20. As noted above, retaining portion 96 is preferably located adjacent to proximal end 26 of shaft 22. The exemplary embodiment of FIG. 3A depicts retaining portion as having four retaining projections 97, equally spaced about the circumference of male driveline interface 28. The bore 68 in shaft receiving part 67 includes a clear space distal to catch ring 92 and projections 93 with a depth 68D along axis B-B. Depth 68D desirably is greater than greater than the axial extent of projections 97 on the male driveline interface (FIG. 3B). The distal end of the bore is defined by a proximal spacer 102 having an opening 101 coaxial with bores 62 and 68 and sized to receive guiding element 36 of male connector 20 described above. The shaft receiving part 67 thus defines an annular shape or rotation path between the distal facing surface 95A of catch projection 93 and proximal spacer 102. As shown in FIG. 10A, catch retaining part 67 also has an anti-rotation element in the form of a pin 63A projecting into this rotation path 68. Anti-rotation element 63A may have a chamfered edge.

The proximal boundary of bore 62 is defined by the proximal spacer 102. The distal end of bore 62 is defined by a distal spacer 100 (FIGS. 6A and 11B). In some embodiments, spacers 100 and 102 may be spaced apart along axis B-B so as to impart a compressive force on bore contacts 70 and seals 80. Because each seal 80 is preferably compressible, this force may serve to maintain each bore contact 70 and seal 80 in a fixed position along axis B-B when potting material 19 is applied.

Distal spacer 100 defines an expansion space 104. (FIG. 11B) Expansion space 104 is in communication with bore 62 via a distal spacer opening 105 within distal spacer 100. Distal spacer opening 105 preferably has a diameter 105D equal or less than diameter 30D of shaft contacts 30. As described above, at least one seal 80 is adapted to seal bore 62 proximal to bore contact 70 when shaft 22 is inserted in bore 62.

The shaft-receiving part 67 of the female connector has a threaded hole 112 extending transverse to the bore 68 of the shaft-receiving part and transverse to the axis B-B. A locking element 110 in the form of a set screw is threaded engaged in the hole. Set screw 110 has a tapered tip 113 at one end and a driving portion 114 with a tool receiving recess 115 shaped to receive a driving tool such as an Allen wrench therein. By turning the set screw 110, the set screw or locking element can be moved between a retracted position depicted in FIGS. 10A and 10B in which the set screw does not project into bore 68 and an engaged position, shown in FIG. 10C, in which the tip 113 of the set screw projects into the bore.

A resilient seal 116 is provided at the end of hole 112 on the exterior surface of the shaft-receiving part 67. Seal 116 is adapted to permit access by a tool to the set screw during the process of engaging the male and female connectors, but to prevent fluid entry into hole 112 after the connectors are engaged with one another. For example, seal 116 may be a resilient element having a slit adapted to receive the driving tool through the slit and then resiliently re-seal hole 112.

Figure 14A:
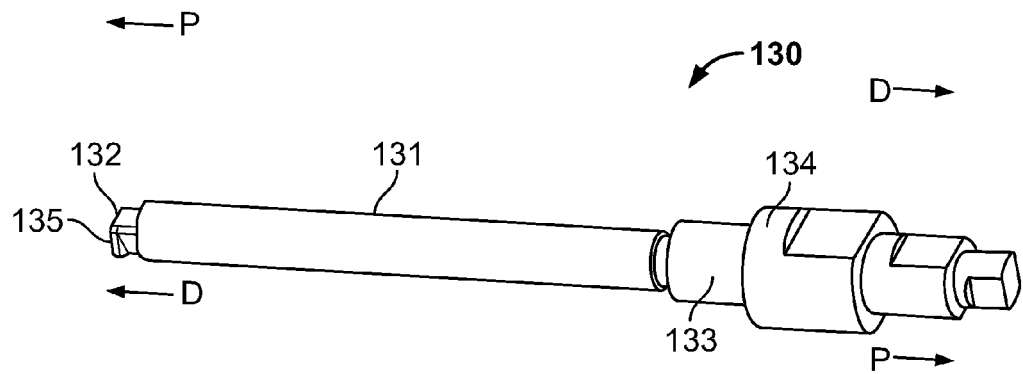
FIGS. 14A-14C are front perspective, front plan, and front sectional views, respectively, of different stages during a method of manufacturing the female connector shown in FIG. 1B.
Figure 14B:
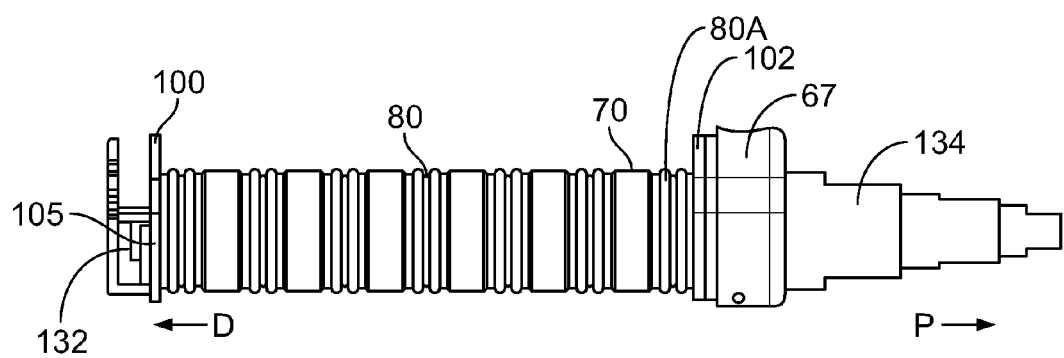
Figure 14C:
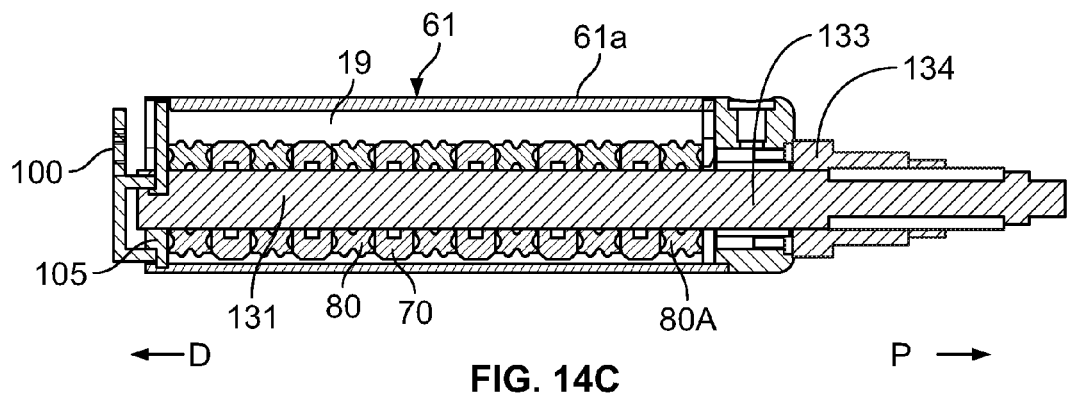

A method of manufacturing female connector 60 is depicted in FIGS. 14A-C. The method uses a female assembly rod 130 having an elongated shaft portion 131 projecting from an interface portion 134. As shown in FIG. 14A, shaft portion 131 preferably has a diameter approximate to diameter 30D of shaft contacts 30 and length greater than that of bore 62. This exemplary method comprises the steps arranging the various elements of female connector 60 on rod 130 as shown in FIG. 14B. The diameter of shaft portion 131 may vary along its length. For example, in FIG. 14A, shaft portion 131 has a distal end 132 sized for insertion into distal spacer opening 105 of distal spacer 100, and a proximal end 133 sized for insertion into the bore of the shaft receiving element 67 and the opening of proximal spacer 102. This configuration desirably permits shaft portion 131 to support each element of female connector 60 during assembly. Furthermore, this configuration also ensures that each element of female connector 60 is coaxially aligned along axis B-B. The distal end 132 of the shaft also has a catch 135 which can releasably engage the distal end spacer 100 and hold it in place.

The bore contacts 70 and seals 80 are arranged on the shaft portion 131 between the distal and proximal spacers 100 and 102. The dimensions of the shaft are selected so that spacers 100 and 102 impart a compressive force on bore contacts 70 and seals 80. Aside from ensuring that each respective element of female connector 60 remains in a fixed position with respect to rod 130, this step also prevents potting material 19 from entering bore 62. Each bore contact 70 is conductively attached to a respective second elongated conductor 16 as discussed above, before or after placement on the rod 130. The conductors are omitted in FIGS. 14A-14C for clarity of illustration. Next, a hollow exterior housing 61a is placed over the elements that have been assembled on rod 130. This creates a void space between the outer surfaces of bore contacts and seals 70, 80, and the interior surfaces of hollow housing 61a, with the conductors disposed in the void space. Preferably, the assembly at this stage includes means for accessing this void space. For example, the housing or one of the other parts may have an access port (not shown) in communication with the void space. As in FIG. 14C, potting material 19 is then used to fill substantially all of the void space via the access port and then cured, thereby sealing and mechanically uniting the various elements of female connector 60 to form the structure 61. After curing, female driveline interface 69 (FIG. 11B) is attached and rod 130 is removed. During introduction of the curing material, the seals 80 compressed between the bore contacts and other elements block passage of the potting material to the inner surfaces of the bore contacts, and assure that the bore of the finished connector is free of potting material.

In a method of engaging the male and female connectors, the shaft 22 of the male connector is inserted through the bore 68 of the shaft-receiving part 67 and into the proximal end of the bore 62 in the female connector. As the distal end of the shaft 22 reaches the proximal end seal 80A, the shaft sealingly engages the proximal end seal. At this stage, the male and female connectors cooperatively define a sealed volume which includes all of the space within the bore 62 distal to the proximal end seal, and which also includes the space 104 (FIG. 11B) in the distal spacer 102. This sealed volume is initially filled with air at atmospheric pressure. As the shaft 22 of the male connector continues to advance into bore 62, the shaft occupies a progressively greater portion of the space within the sealed volume and the air within the sealed volume is compressed. The compressed air acts on the shaft and creates a force opposing further insertion. When the shaft is fully advanced, the final absolute air pressure $P_F$ in the sealed volume will be approximately:

$$P_F = P_A * (V_{SV})/(V_{SV} - V_{SH})$$

Where:

$P_A$ is atmospheric pressure;

$V_{SV}$ is the volume within the sealed volume; and $V_{SH}$ is the volume of the shaft which is inserted into the sealed volume, i.e., the volume of the shaft which lies distal to the proximal end seal 80A when the shaft is fully inserted. Because the sealed volume $V_{SV}$ is larger than $V_{SH}$, the air pressure does not reach extreme levels. $V_{SV}$ can be sized to provide any desired value of final pressure $P_F$. For example, ISO27186, an international standard for medical device connectors, specifies a maximum insertion force of 16N or 3.59 lb-f. For an embodiment of shaft 22 having a diameter of about 3 mm, a pressure of 288 lb/in$^2$ corresponds to a force of 16N exerted by the compressed air to provide a final pressure $P_F$ less than this. Thus, the value of $(V_{SV} - V_{SH})$ must be at least 1.05 times $V_{SH}$. Larger values of $V_{SV}$ are also possible, such as at least 1.0 times $V_{SH}$, or at least about 1.2 to 1.3 times $V_{SH}$, to provide even lower pressure values.

During insertion, the locking element 110 is in the retracted position shown in FIG. 10A, where the locking element is clear of the bore 68 in the shaft-receiving piece 67 of the female connector. The axes of the male and female connectors are coincident, and lie along common axis BA-BA. The male connector is brought to a first rotational position about the axis relative to the female connector. In this first rotational position, depicted in FIG. 10A, the projections 97 on the male interface adaptor, which constitute the retaining elements of the male connector, are out of alignment with the projections 93 of the female connector, which constitute catch elements. In this first position, the retaining elements or projections 97 are aligned with the grooves 94 of the female connector. While the connectors are in this first rotational position, the male connector is advanced distally to its fully-inserted position. The retaining elements or projections 97 pass through grooves 94, from the proximal side of the catch elements or projections 93 on the female connector to the distal side of projections 93.

Figure 10B:
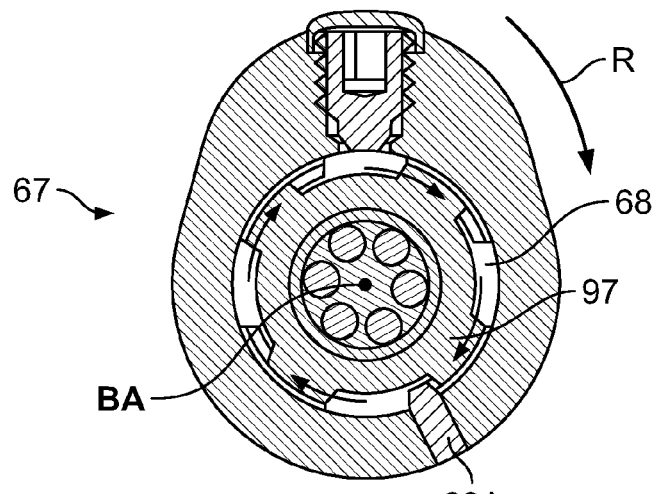

Once the male connector has reached this position, the male connector can be rotated relative to the female connector, as indicated by arrow R in FIG. 10B, until it reaches the second rotational position shown in this figure. In the second rotational position, the retaining elements or projections 97 of the male connector are aligned with the catch elements or projections 93 of the female connector. A proximal facing surface 98B of each retaining element 97 (FIGS. 3A and 4) confronts a distal facing surface 95A of each catch element 93 (FIGS. 9A and 4) when shaft 22 is in the second position. At this point, shaft 22 is retained in bore by the interaction of retaining elements 97 and catch elements 93. Anti-rotation element 63A ensures proper alignment of retaining elements 97 with catch elements 93 by stopping rotation of the male connector at the second position.

Figure 10C:
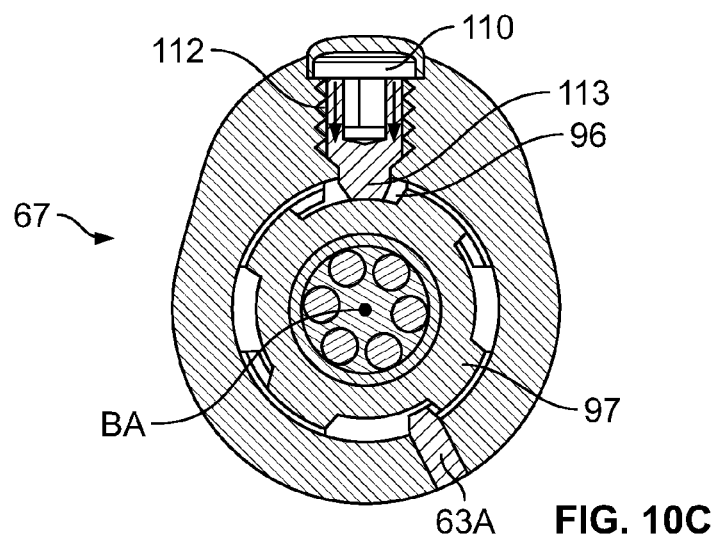

Locking element 110 may be engaged once shaft 22 is in the second rotational position. As shown in FIG. 10C, the locking element or setscrew 110 projects into the bore when the locking element is in the engaged position. As best appreciated with reference to FIG. 4, the locking element 110 is aligned, along the common axis BA, with retaining portion 96 of male connector 20 and with projections 97 on the male connector. Rotation of the male connector in the reverse direction (opposite to arrow R in FIG. 9B) is blocked by interference between the locking element 110 and the retaining elements or projections 97. The male connector is thus securely locked against withdrawal from the female connector. Set screw 111 may be tightened sufficiently to frictionally engage tip 113 with retaining portion 96. Importantly, however, the connectors remain securely locked even if tip 113 is not frictionally engaged as long as tip 113 lies within the rotation path of the projections. In this configuration, retention means 90, including the retaining elements 97 and catch elements 93, prevents any substantial translation of shaft 22 along axis BA-BA, while locking element 100 prevents any substantial rotation of shaft 22 about axis BA-BA.

When the male connector is in its fully advanced position, each shaft contact 30 is engaged with one bore contact 70 so that the wires of the first and second drivelines are conductively connected to one another through the engaged connectors. Also, the seals 80 sealingly engage the shaft 22 of the male connector. In this fully engaged condition, guiding element 36 of the male connector is engaged in the opening 101 of the proximal spacer 102 in the female connector. (See FIG. 11A) so that the guiding element helps maintain concentricity of the shaft 22 and bore 62. Also, in the fully engaged condition, the edge 43 of the overmold 42 on the male connector (FIG. 4) abuts the shaft-receiving piece 67 of the female connector to form a seal.

Figure 15:
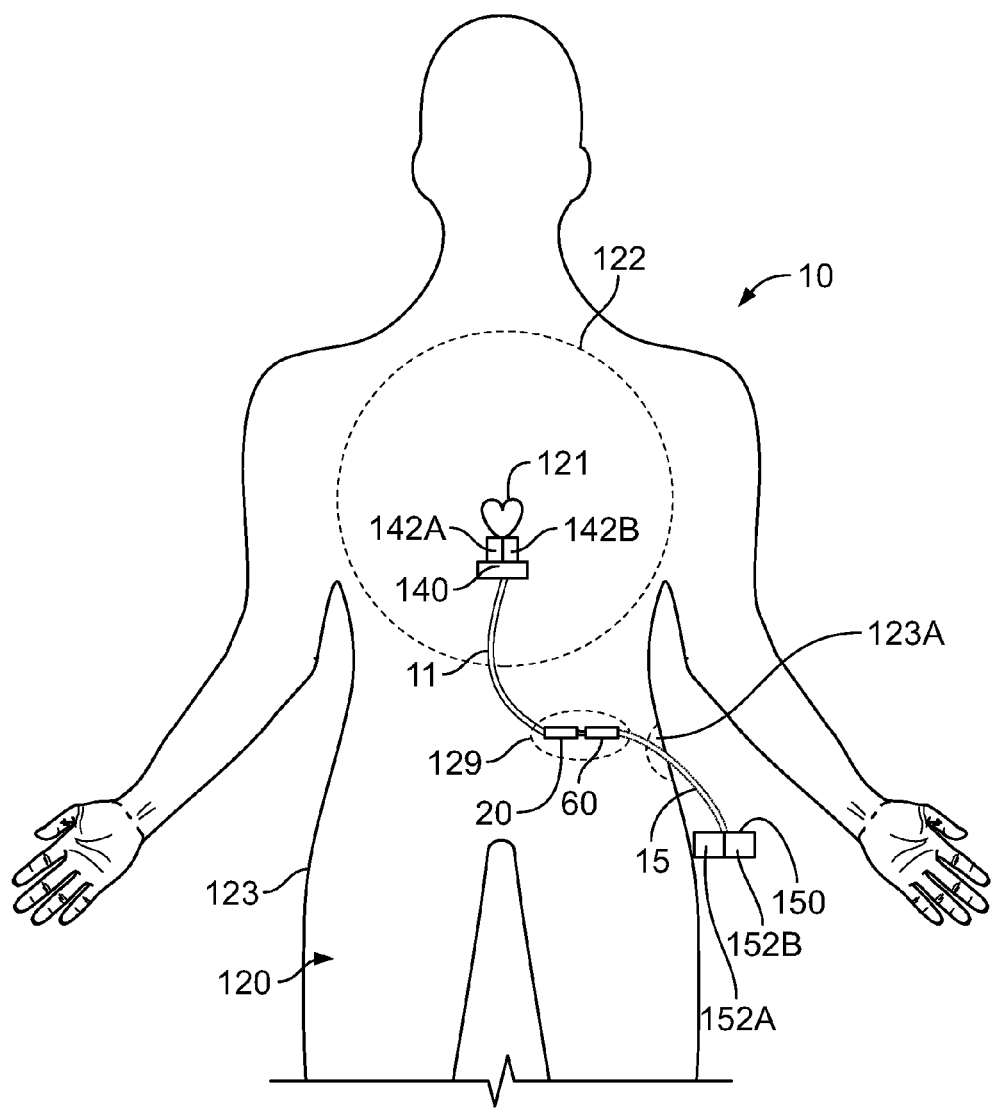
FIG. 15 is a front plan view of a connection system having an implanted medical device in accordance with an embodiment of the present invention.

The connectors 20, 60 can be used as elements of an implanted system. A system 10 is described below as a further embodiment of the invention. System 10 is depicted in FIG. 15 has having an implanted medical device 140, such as a ventricular assist device or VAD device 140. In this embodiment, device 140 has two elements which are at least partially redundant. For example, the VAD device 140 of FIG. 15 includes a first set of electrical coils schematically indicated at 142A and a second set of electrical coils schematically indicated at 142B. The first set of coils is arranged to drive a first rotor (not shown) within the device 140, whereas the second set of coils is arranged to drive a second rotor (not shown) within the device 140. In normal operation, both rotors operate. However, the VAD device 140 will still pump enough blood to keep a patient alive even if only one rotor is operational. VAD device 140 is connected to male connector 20 through the first driveline 11. Most preferably, the first redundant element (coil set 142A) is connected by certain conductors in first driveline 11 to the first set 30A of the shaft contacts 30 disposed adjacent the proximal end 26 of shaft 22 of male connector 20 (FIG. 1A). The second redundant element 142B is independently connected through other conductors of the first driveline 11 to the second set of shaft contacts 30B disposed adjacent the distal end 24 of shaft 22. The assembly of the implantable device 140 and the first driveline 11 may include a permanent or semi-permanent connection between device 140 and driveline 11 that is formed by the manufacturer or made by any suitable method before or during the implantation procedure discussed below.

The system 10 further includes a source of electrical power, such as external controller 150. Controller 150 desirably includes redundant circuits such as a first drive circuit 152A arranged to supply electrical power to the first set of coils 142A and a second drive circuit 152B arranged to supply electrical power to the second set of coils 142B. Controller 150 is connected to the female connector 60 by second driveline 15. Desirably, the first circuit 152A is connected to the first set 70A of the bore contacts 70 (FIG. 6A) adjacent the proximal end 66 of the bore 62, whereas the second circuit 152B is connected to the second set 70B of bore contacts adjacent the distal end 64 of bore 62 and distal to the center seal 80C.

VAD device 140 is implanted within a living body 120 such as a human body 120 having a thorax 122 and an exterior skin 123. As is commonly understood, the thorax 122 includes any portion of human body 120 that is situated between the neck and the abdomen, and supported by the ribs, costal cartilages, and sternum. Heart 121 of body 120 is contained within a pericardial sac contained within of thorax 122. VAD device 140 is implanted in body 120, preferably in close proximity to heart 121 and within the thorax 122. In some embodiments, device 140 is adjacent heart 121 and within the pericardial sac. Once device 140 is implanted, male connector 20 may be located at an internal connection point 129 disposed away from heart 121. Preferably point 129 is at least outside of the pericardial sac, or even outside of thorax 122. Female connector 60 may be located at the internal connection point 129 by any known means. For example, female connector 60 may be pulled through a surgically-formed tunnel through body 121 to arrive at internal connection point 129. Second driveline is implanted so that the female connector 60 is also present at the internal connection point 129, and so that the second driveline 15 extends through the exterior skin 123 of body 120 at a skin opening 123A. Desirably, the internal connection location 129 is close to skin opening 123A, but not directly at the opening.

In FIG. 15, female connector 60 is releasably coupled to male connector 20 at internal connection point 129 so as to operatively connect first and second drivelines 11, outside of the thorax 122. The connectors are locked together as discussed above. Once this connection is made, and preferably locked via locking element 100, external device 130 is operationally connected to the implanted device 120 via a composite driveline formed by connecting the first and second drivelines 11 and 15 at internal connection point 129. The surgical openings used for implantation and for access to connection site 129 are closed.

Advantageously, should skin opening 123A become infected, the infection can be remedied by a minor surgical procedure. Connection point 129 is accessed to expose the connectors 20 and 60, which are then disconnected. A new third driveline (not shown) with a new female connector is connected to implanted male connector 20 at point 129. The new driveline is routed through the skin and out of body 120 at a new skin opening that is remote from the now infected skin opening 123A. Advantageously, this procedure can be performed without entering the thorax 122 (or the pericardium sac, depending upon the location of point 129). In comparison to the operation which would be required to replace the entire composite driveline, this constitutes a relatively minor surgery. For example, the exemplary method set forth above does not require any re-tunneling of first driveline 11 through the body 120.

Connectors 20 and 60 also provide a significant safety benefits. As mentioned above, the second set of bore contacts 70B (FIG. 6A) are disposed distal to the center seal 80C. When connectors 20 and 60 are assembled, the second set of shaft contacts 30B is aligned with the second set of bore contacts 70B, so that the connections between the second sets of bore and shaft contacts, 30B and 70B respectively, are also distal to the center seal 80C. In normal operation, the proximal end seal 80A excludes body fluids from the entire bore, so that all of the connections between the each of the first and second sets of contacts 30A, 70A and 30B, 70B remain functional. If the proximal end seal 80A fails, one or more of the connections between the first set of contacts 30A, 70A may fail. Consequently, the first set of coils 142A in the VAD device 140 may cease to operate or may operate at reduced efficiency. The second set of coils 152B, however, will remain functional so that VAD device 140 can provide enough blood flow to keep the patient alive. Moreover, the failure of coils 142A may be detected by appropriate monitoring circuitry in external controller 150 so that the patient can seek attention to correct the failure. In the particular embodiment depicted, where there are further seals 80 between the proximal end seal 80A and the center seal 80C, these additional seals 80 provide still further safety. For example, these additional seals 80, as well as the center seal 80C, also must fail before the second set of contacts 30B and 70B will remain fail. Therefore, VAD device 140 may continue to sustain life, even if seal 80A fails, by drawing power from source 150 via the second set of contacts 30B, 70B.

The features discussed above can be varied without departing from the present invention. Some of these variants are discussed separately below. However, the elements of any of these variants and alternate embodiments might also be incorporated into any embodiment of any connector, method or system described anywhere in the text of this application.

In the system discussed above with reference to FIG. 15, the male connector 20 may be coupled to the controller 150 and the female connector may be coupled to the implanted device 140. Although described with reference to an exemplary VAD device 140, connectors 20 and 60 can be used to provide power or signals to or from an implanted device of any nature. In the VAD embodiment discussed above, the first and second coil sets 142A and 142B 120b are redundant, in that either element can sustain life. However, the elements connected through the first and second sets of contacts 30A, 70A and 30B, 70B need not be redundant. For example, the second set of contacts 30B, 70B may be connected to an essential element of a device, whereas the first set of contacts 30A, 70A, which are adjacent to the proximal end 66 of the bore 62, may be connected to a non-essential element such as a monitoring or control system.

In some embodiments, the elements of the retention means may be adapted to provide a means for keying a particular male connector to a particular female connector. For example, the catch ring 92 (FIG. 9A) may have a shape that is only engageable with a correspondingly shaped retaining portion 96 (FIG. 3A). By way of example, the catch rings of some female connectors may be made with catch rings having three equally-spaced projections 93 and three grooves 94, and the corresponding retaining portion 96 may have three equally-spaced projections 97. Still other variants can have unequally spaced projections and grooves in unique patterns. This is useful in assuring proper connections where there are multiple interconnects in any given system. The keyed shapes may be defined exclusively by the geometric arrangement of grooves 94 about the axis. Alternatively, one or more of the retaining projections and grooves may be of different sizes or shapes, so that it will fit only a correspondingly-shaped groove.

In the embodiments discussed above, the projections or catch elements 93 on the catch ring have distal surfaces 95A (FIG. 9A) which do not slope in the axial direction. However, the catch elements may have surfaces defining a portion of a helix about the axis B-B, so as to define complete or partial screw threads. Here again, the mating retaining elements 97 (FIG. 3A) may also have helical surfaces.

In the embodiments discussed above, the locking element or set screw 110 (FIGS. 9A-9B) moves radially towards the axis as it is moved from its retracted position to its advanced position. However, the locking element may move in other directions, such as directions parallel to the axis. Also, the locking element need not be a screw. For example, the locking element may be a pin, and may be held in its advanced or locking position be another element. Also, the seal associated with the locking element may be omitted or may be varied.

The swage caps 32 (FIGS. 2A and 7A) may be omitted where the metal of the wires is compatible with the metal of the contacts, so as to allow direct welding. Alternatively, the swage caps can be replaced by jumper wires. In this embodiment, one end of each jumper wire is conductively attached to a contact 30 or 70, while the opposite end of the jumper wire is conductively attached to terminus 13 or 17 of first or second elongated conductors 12 or 16 at a point remote from the respective contacts 30 or 70.

Figure 12:
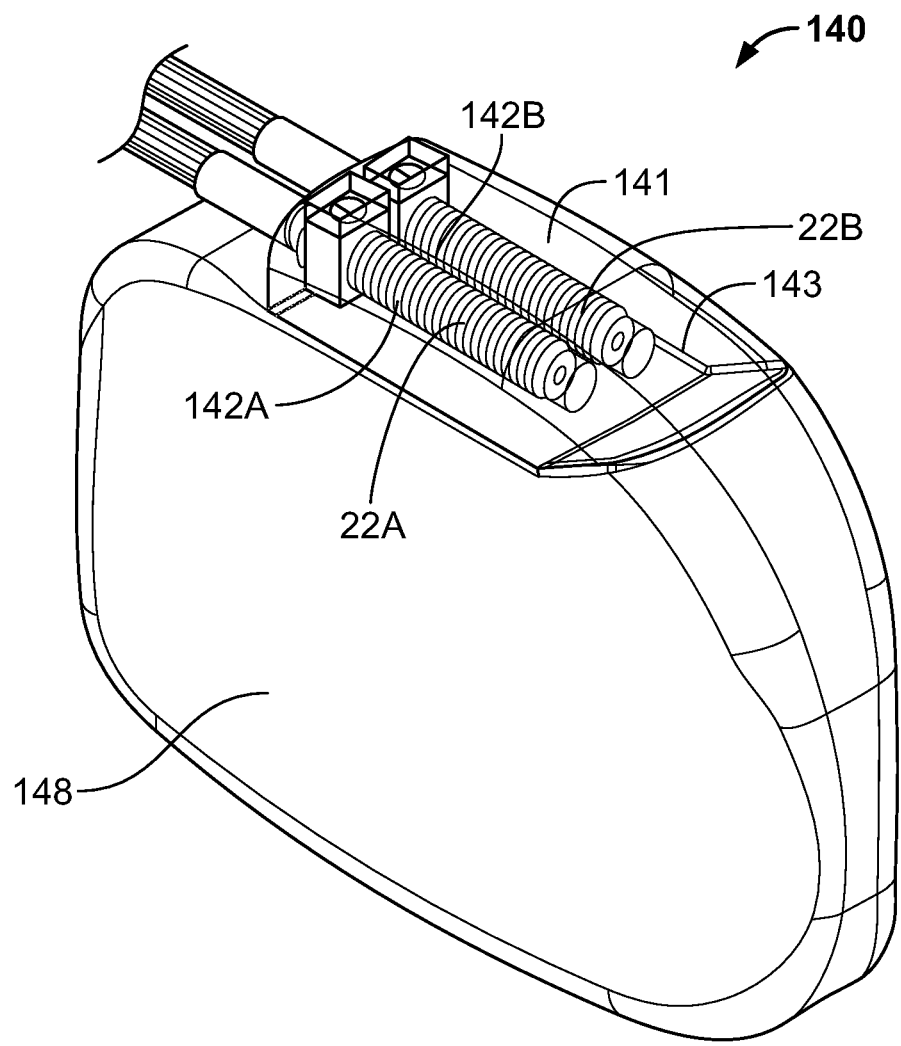
FIG. 12 is a front perspective view of a female connector in accordance with another embodiment of the present invention.

The connectors need not be attached to drivelines as discussed above. For example, as shown in FIG. 12, a female connector 140 has a structure 141 that is integral with a portion of an implantable device 148, such as header 143. Header 143 may be adapted to embody any or all of the features and capabilities of structure 61 discussed herein. For example, an exemplary connection system 10 might include an implantable device 148 with a bore 142 housed within header 143. FIG. 12 also demonstrates that header 143, or any embodiment of structure 61 for that matter, may alternatively be adapted to include a first bore 142A adapted to receive a first shaft 22A and a second bore 142B adapted to receive a second shaft 22B.

Figure 8C:
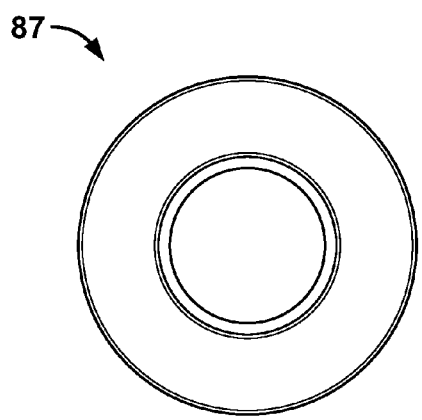
FIGS. 8C and 8D are front plan and side sectional views, respectively, of a secondary seal used in connection with the female connector shown in FIG. 1B.
Figure 8D:
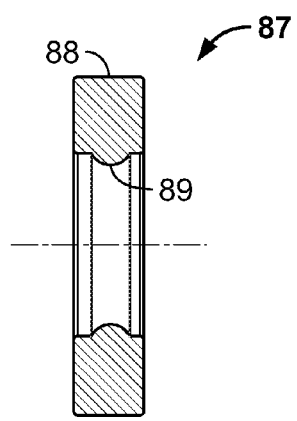

A variety of seals may be utilized. For example, a female connector may incorporate two different types of seals a primary seal equivalent to seal 80, as shown in FIGS. 8A-B; and a secondary seal 87, as shown in FIGS. 8C-D. The secondary seal may be thinner and may be less resistant to leakage than the primary seal. The primary seal may be provided at the proximal end of the bore, whereas secondary seals may be used at other locations distal to the primary seal. In a variant of this approach, a primary seal is also used at a location between different sets of contacts, so as to provide enhanced reliability in the event of primary seal failure. In a variant of this approach, the secondary seals may be replaced by dielectric washers which separate adjacent contacts from one another but which do not seal against fluid leakage along the shaft. Such washers may seal against entry of the potting material between the bore contacts during the manufacturing process discussed above with reference to FIGS. 14A-14C. In a further variant, the manufacturing process can be varied so that potting material 19 may alternatively extends between adjacent bore contacts so as to eliminate the need for separate seals or washers between the bore contacts. This would require measures during the manufacturing process to avoid contamination of the interior surfaces of the bore contacts by the potting material. Alternatively still, potting material 19 may be utilized to define the boundaries of expansion space 104.

In the embodiments discussed above, the seals are carried on the structure of the female connector. However, some or all of the seals may be carried on the male connector as, for example, as O-rings surrounding the shaft.

The varied connection types of connection system 10 also permit optimization of connector type, either male or female, with device type. For example, any system or method employing connection system 10 may be adapted provide the less replaceable, more critical device with male connector 20 as it is easier to clean than female connector 60 in the event it becomes contaminated during placement or use.

Figure 16:
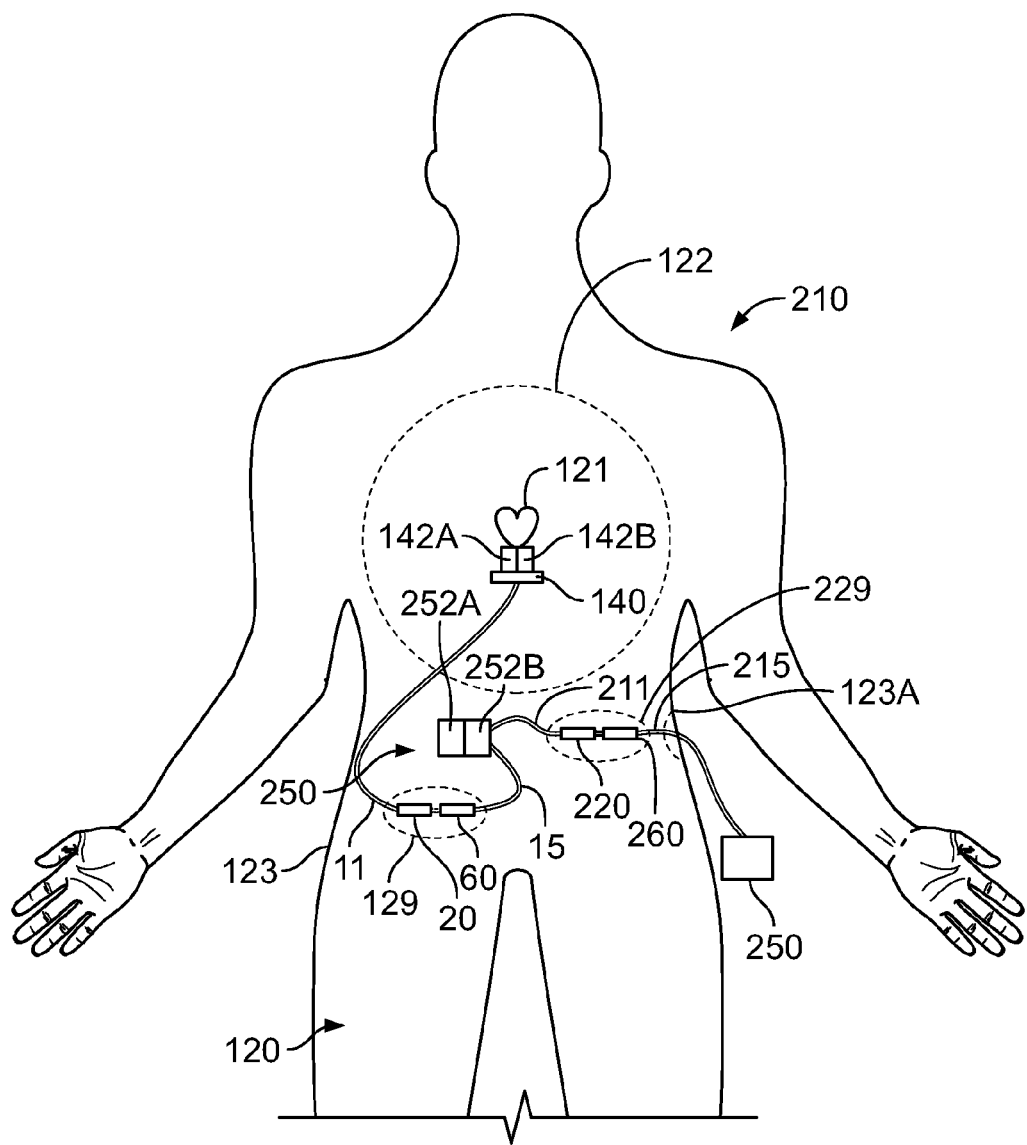
FIG. 16 is a front plan view of a connection system having an implanted medical device in accordance with another embodiment of the present invention.

Multiple sets of connectors 20 and 60 may also be deployed within a system 210 that, as shown in FIG. 16, includes an implantable controller 250. Much like external controller 150, the implantable controller 250 has a first set of circuits 252A and a second set of circuits 252B. As before, first and second drivelines 11 and 15 are attached by connectors 20 and 60 to form a first composite driveline. This allows controller 250 to power the first set of circuits 252A with the first set of contacts 30A, 70A and the second set of circuits 252B with the second set of contacts 30B, 70B. In contrast to above, however, implantable controller 250 is also connected to an external device or power source 150 by a second composited driveline form by connecting first and second drivelines 211 and 215 at an internal connection point 229 using male and female connectors 220 and 260. Connectors 20 and 60 are identical to connectors 220 and 260, except in the 200 series of numbers. Therefore, the benefits described above with reference to FIG. 15 may be further extended in system 210. For example, the second driveline 215 may also be replaced with a new third driveline (not shown) during a minor surgical procedure because driveline 215 also exits through the skin opening 123A in a similar manner to driveline 15. As a further example, the first and second circuits 252A, 252B of controller 250 can be also powered with a corresponding set of first and second set of contacts 230A, 270A and 230B, 270B within connectors 220 and 260. Aside from these redundancy benefits, this configuration also allows implantable controller 250 to be easily replaced or upgraded to enhance patient safety. For example, each internal connection points 129 and 229 may be adjacently located outside of thorax 122 so that implantable connector 250 can be removed in a single procedure, preferably using common surgical opening.

In a further variant, the connections discussed above can be used to make internal connections within a system that is entirely implanted under exterior skin 123, thereby eliminating the need for skin opening 123A. For example, connectors 20 and 60 may be used to connect device 140 to implanted controller 250, as in FIG. 16, while connectors 220 and 260 are used to connect controller 250 to another power source. In such a system, for example, controller 150 may be powered by a transcutaneous energy transfer coil or TET coil that is implanted beneath skin 123 at some point in body 120. Once implanted, the TET coil is adapted to receive power from an external coil adjacent skin 123. Because there is no skin opening 123A, the risk of infection in this alternate system is reduced. Nonetheless, by connecting the TET coil to the implanted controller 250 with connectors 220 and 260 at an internal connection point like points 129 or 229 described above, similar benefits can be realized. For example, the system controller 250 may be redundantly connected to the TET coil, which, like controller 250, may also be easily replaced as part of relatively minor surgical procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A connection system implantable within a living body having an exterior skin, comprising:
  (I) a male connector with:
    a shaft extending along an axis between a proximal end and a distal end, the shaft having an exterior surface surrounding the axis;
    at least one shaft contact carried on the shaft and exposed at the exterior surface; and
    a retaining element mounted to the shaft; and
  (II) a female connector with:
    a structure defining a bore extending along an axis between a proximal end and a distal end;
    at least one bore contact mounted to the structure and exposed within the bore; and
    a catch element mounted to the structure,
  wherein the catch and retaining elements are constructed and arranged so that the shaft can be inserted into the bore along the axis of the bore to align the at least one shaft contact with the at least one bore contact,
  wherein the shaft can be inserted in the bore in a first position in which the retaining element is offset from the catch element and retained in the bore when rotated about the axis of the bore into a second position in which the retaining element is aligned with the catch element, and
  wherein a locking element is mounted to one of the shaft and the structure, the locking element being movable between an unlocked position in which the shaft can be rotated about the axis of the bore and a locked position in which the locking element prevents rotation of the shaft relative to the structure.

2. The system of claim 1, wherein the bore is closed at its distal end and the male and female connectors are constructed and arranged to seal the bore proximal to the at least one bore contact when the shaft is inserted in the bore.

3. The system of claim 2, wherein the male and female connectors cooperatively define a sealed interior volume when the shaft is inserted in the bore, wherein the sealed interior volume is at least about 1.10 times the volume of the shaft disposed within the sealed volume when the male and female connectors are fully engaged with one another.

4. The system of claim 3, wherein the structure defines an expansion space in communication with the bore, and wherein the expansion space is at least about 0.05 times the total interior volume.

5. The system of claim 1, wherein the catch element includes a catch ring with proximal and distal surfaces extending at least partially around the axis of the bore, the catch ring having at least one groove extending from the proximal surface to the distal surface, and wherein the retaining element includes at least one projection extending away from the exterior surface of the shaft transverse to the axis of the shaft such that the at least one projection can be inserted through the at least one groove.

6. The system of claim 5, further comprising an anti-rotation element mounted to the structure and disposed distal to catch ring, the anti-rotation element configured to engage the at least one projection to limit rotation of the shaft relative to the structure.

7. The system of claim 1, wherein the structure defines a hole extending into the bore transverse to the axis of the bore, and wherein the locking element is engageable with the male connector through the hole to lock the shaft against rotation relative to the structure.

8. The system of claim 7, wherein the locking element is a set screw and the hole has a threaded wall, and wherein a driving portion of the set screw is covered by a set screw seal adapted to receive a tool engageable with the driving portion.

9. The system of claim 1, wherein either the shaft or the bore has at least one seal adapted to seal the bore proximal to the at least one bore contact when the shaft is inserted in the bore.

10. The system of claim 9, wherein the at least one shaft contact includes a first set of shaft contacts spaced apart from a second set of shaft contacts along the axis of the shaft and the at least one bore contact includes a first set of bore contacts spaced apart from a second set of bore contacts along the axis of the bore, wherein insertion of the shaft into the bore along the axis of the bore aligns the first and second sets of shaft contacts with the respective first and second sets of bore contacts.

11. The system of claim 10, further comprising an intermediate seal on either the shaft or the bore, the intermediate seal being disposed between the first and second sets of shaft and bore contacts when the shaft contacts are aligned with the bore contacts.

12. The system of claim 11, wherein each of the first and second sets of shaft contacts and each of the first and second sets of bore contacts includes three contacts.

13. The system of claim 12, wherein either the shaft or the bore has at least one seal located between each mutually adjacent shaft or bore contact.

14. The system of claim 11, further comprising an implanted medical device having first and second elements, the second element being sufficient to sustain life, and wherein the first element is connected to the first sets of shaft and bore contacts and the second element is connected to the second sets of shaft and bore contacts.

15. The system of claim 14, wherein each of the first and second elements is a pump having a motor.

16. The system of claim 1, wherein the at least one shaft contact is an outer ring and the at least one bore contact is an inner ring, and wherein the inner ring is coaxially aligned with the outer ring when the male connector is inserted into the female connector.

17. The system of claim 16, further comprising an elongated conductor with a terminus attached to each of the at least one bore contacts and the at least one shaft contacts, wherein each terminus is welded to a respective swage cap that is conductively attached to the respective elongated conductor.

18. The system of claim 16, wherein each of the at least one bore contacts has an interior surface with an annular groove and a spring element disposed in the annular groove so as to conductively engage one of the at least one shaft contacts.

19. A connection system implantable within a living body having a thorax and an exterior skin, comprising:
- a first driveline extending between an implantable device configured to be located inside the thorax and a first connector configured to be located at an internal connection point disposed outside of the thorax; and
- a second driveline configured to extend through the exterior skin between an external device located outside the body and a second connector that is configured to be releasably coupled to the first connector at the internal connection point so as operatively connect the first and second drivelines,
- wherein the first connector can be decoupled from the second connector at the internal connection point.

20. The system of claim 19, wherein the internal connection point is disposed outside of the pericardial sac.

21. The system of claim 19, wherein the implanted device is a medical device having at least two partially redundant elements, each element being sufficient to sustain life, wherein each of the first and second connectors has a first set of contacts sealed independently from second set of contacts, and wherein each of the at least two partially redundant elements is powered by one of either the first or second sets of contacts.

22. The system of claim 21, wherein the second driveline is configured to extend between the second connector at the internal connection point and a third connector adapted for mounting at the skin.

* * * * *